(12) United States Patent
Podack et al.

(10) Patent No.: US 8,685,384 B2
(45) Date of Patent: *Apr. 1, 2014

(54) RECOMBINANT CANCER CELL SECRETING MODIFIED HEAT SHOCK PROTEIN-ANTIGENIC PEPTIDE COMPLEX

(75) Inventors: Eckhard R. Podack, Coconut Grove, FL (US); Julie Spielman, Miami, FL (US); Koichi Yamazaki, Miami, FL (US)

(73) Assignee: University of Miami, Miami, FL (US)

( * ) Notice: Subject to any disclaimer, the term of this patent is extended or adjusted under 35 U.S.C. 154(b) by 1008 days.

This patent is subject to a terminal disclaimer.

(21) Appl. No.: 11/878,460

(22) Filed: Jul. 24, 2007

(65) Prior Publication Data

US 2008/0026012 A1 Jan. 31, 2008

Related U.S. Application Data

(62) Division of application No. 09/253,439, filed on Feb. 19, 1999, now abandoned.

(60) Provisional application No. 60/075,358, filed on Feb. 20, 1998.

(51) Int. Cl.
| | |
|---|---|
| *A01N 63/00* | (2006.01) |
| *A61K 48/00* | (2006.01) |
| *A01N 65/00* | (2009.01) |
| *A61K 39/00* | (2006.01) |

(52) U.S. Cl.
USPC .... 424/93.1; 424/93.21; 424/93.7; 424/277.1

(58) Field of Classification Search
None
See application file for complete search history.

(56) References Cited

U.S. PATENT DOCUMENTS

| | | | |
|---|---|---|---|
| 4,690,915 A | 9/1987 | Rosenberg | |
| 5,188,964 A | 2/1993 | McGuire et al. | |
| 5,217,891 A * | 6/1993 | Brake et al. | 435/226 |
| 5,232,833 A | 8/1993 | Sanders et al. | |
| 5,348,945 A | 9/1994 | Berberian et al. | |
| 5,719,044 A | 2/1998 | Shoseyov et al. | |
| 5,747,332 A | 5/1998 | Wallen et al. | |
| 5,750,119 A | 5/1998 | Srivastava et al. | |
| 5,830,464 A | 11/1998 | Srivastava | |
| 5,837,251 A | 11/1998 | Srivastava | |
| 5,948,646 A | 9/1999 | Srivastava | |
| 5,961,979 A | 10/1999 | Srivastava | |
| 5,985,270 A | 11/1999 | Srivastava | |
| 5,997,873 A | 12/1999 | Srivastava | |
| 6,007,821 A * | 12/1999 | Srivastava et al. | 424/193.1 |
| 6,017,540 A | 1/2000 | Srivastava et al. | |
| 6,017,544 A | 1/2000 | Srivastava | |
| 6,030,618 A | 2/2000 | Srivastava | |
| 6,048,530 A | 4/2000 | Srivastava | |
| 6,130,087 A | 10/2000 | Srivastava et al. | |
| 6,136,315 A | 10/2000 | Srivastava | |
| 6,156,302 A | 12/2000 | Srivastava | |
| 6,162,436 A | 12/2000 | Srivastava | |
| 6,168,793 B1 | 1/2001 | Srivastava et al. | |
| 6,322,790 B1 | 11/2001 | Srivastava | |
| 6,328,957 B1 * | 12/2001 | Colston et al. | 424/93.2 |
| 6,331,299 B1 | 12/2001 | Rothman et al. | |
| 6,383,493 B1 | 5/2002 | Srivastava et al. | |
| 6,383,494 B1 | 5/2002 | Srivastava et al. | |
| 6,387,374 B1 | 5/2002 | Srivastava et al. | |
| 6,399,070 B1 | 6/2002 | Srivastava et al. | |
| 6,403,095 B1 | 6/2002 | Srivastava et al. | |
| 6,406,700 B1 | 6/2002 | Srivastava | |
| 6,410,026 B1 | 6/2002 | Srivastava | |
| 6,410,027 B1 | 6/2002 | Srivastava | |
| 6,410,028 B1 | 6/2002 | Srivastava | |
| 6,436,404 B1 | 8/2002 | Srivastava et al. | |
| 6,447,780 B1 | 9/2002 | Srivastava et al. | |
| 6,447,781 B1 | 9/2002 | Srivastava | |
| 6,451,316 B1 | 9/2002 | Srivastava | |
| 6,455,048 B1 | 9/2002 | Srivastava et al. | |
| 6,455,503 B1 | 9/2002 | Srivastava | |
| 6,461,615 B1 | 10/2002 | Srivastava | |
| 6,468,540 B1 | 10/2002 | Srivastava | |
| 6,475,490 B1 | 11/2002 | Srivastava et al. | |
| 6,605,464 B1 | 8/2003 | Rothman et al. | |
| 6,610,659 B1 | 8/2003 | Pramod | |

(Continued)

FOREIGN PATENT DOCUMENTS

| | | |
|---|---|---|
| CA | 2158655 | 9/1994 |
| DE | 196 02 985 A1 | 7/1997 |

(Continued)

OTHER PUBLICATIONS

Ezzell (J. Nih Res, 1995, 7:46- 49).*
Spitler (Cancer Biotherapy, 1995, 10:1-3).*
Boon (Adv Can Res, 1992, 58:177-210).*
DeGruijl et al (Nature Medicine, 5410): 1124-1125, Oct. 1999).*
Bodey et al (Anticancer Research. 20:2665-2676; 2000).*
Gaiger et al (Blood, vol. 96, No. 4, Aug. 2000, pp. 1480-1489).*
Zinn et al (Proc. Natl. Acad Sci. 1982 79:4897).*
Philip et al., Mol. Cell. Biol. 1994, 14(4): 2411-2418.*
Yamazaki et al., J Allergy Clin Immuno., Jan. 1997, 99 (1 Pt2): S1-738, Abstract No. 187.*

(Continued)

*Primary Examiner* — Hong Sang
(74) *Attorney, Agent, or Firm* — Fish & Richardson P.C.

(57) ABSTRACT

The present invention relates to methods for purifying immunogenic, prophylactically and therapeutically effective complexes of modified heat shock proteins noncovalently associated with antigenic peptides of cancer or infected cells. The claimed methods comprise the constructing of a nucleotide sequence encoding a secretable modified heat shock protein, expressing the sequence in an appropriate host cell, recovering the immunogenic complexes from the cell culture and the cells, and purifying the immunogenic complexes by affinity chromatography. Large amounts of such immunogenic complexes can be obtained by large-scale culturing of host cells containing the genetic sequence. The complexes can be used as a vaccine to elicit specific immune responses against cancer or infected cells, and to treat or prevent cancer or infectious diseases.

16 Claims, 6 Drawing Sheets

(56) References Cited

U.S. PATENT DOCUMENTS

Figure 1C:
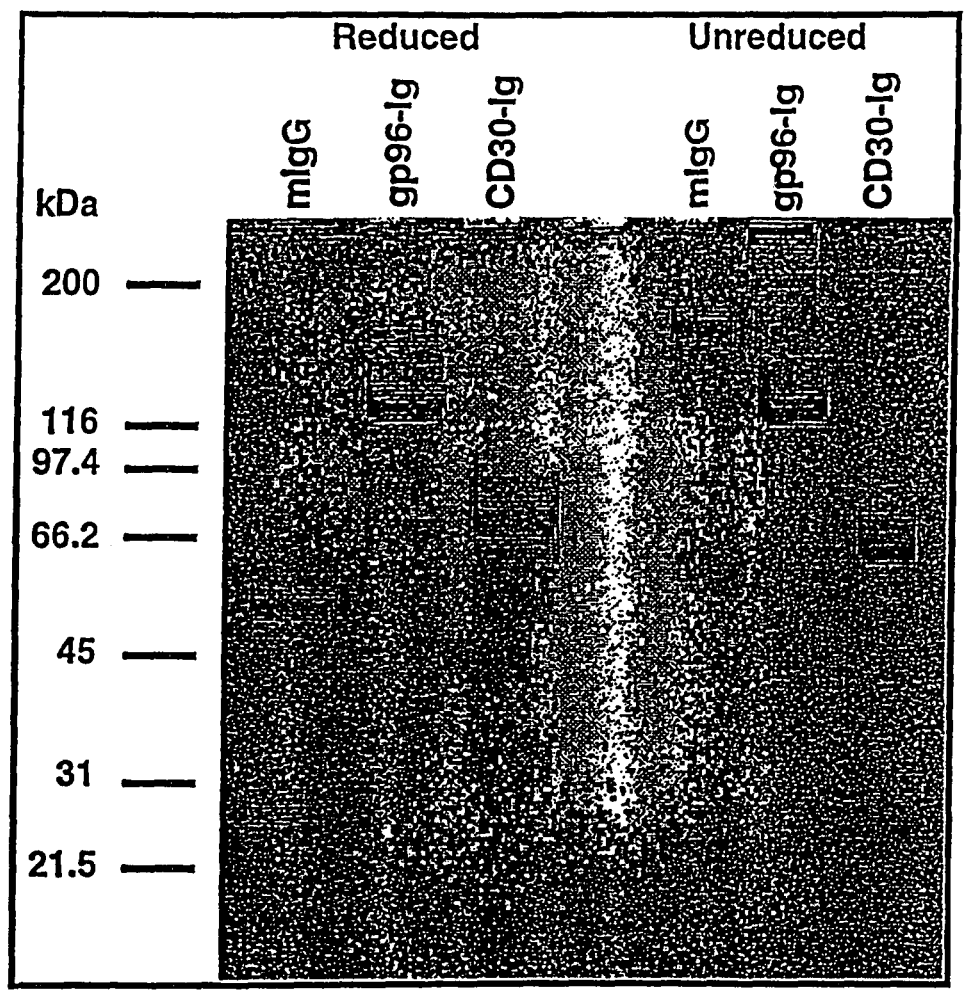

| | | |
|---|---|---|
| 6,641,812 B2 | 11/2003 | Rothman et al. |
| 6,656,679 B2 | 12/2003 | Rothman et al. |
| 6,663,868 B1 | 12/2003 | Rothman et al. |
| 6,673,348 B2 | 1/2004 | Rothman et al. |
| 6,719,974 B1 | 4/2004 | Rothman et al. |
| 6,761,892 B1 | 7/2004 | Rothman et al. |
| 6,797,480 B1 | 9/2004 | Srivastava |
| 7,132,109 B1 | 11/2006 | Srivastava |
| 2003/0170756 A1 | 9/2003 | Berd |
| 2005/0019752 A1 | 1/2005 | Franchini |
| 2007/0141666 A1 | 6/2007 | Dupraz |
| 2008/0019972 A1 | 1/2008 | Andrieu |
| 2008/0089901 A1 | 4/2008 | Hanke |
| 2009/0162404 A1 | 6/2009 | Podack |
| 2011/0171211 A1 | 7/2011 | Podack |
| 2011/0250229 A1 | 10/2011 | Podack |

FOREIGN PATENT DOCUMENTS

| | | |
|---|---|---|
| GB | 2 251 186 | 7/1992 |
| WO | WO 89/12455 | 12/1989 |
| WO | WO 90/02564 | 3/1990 |
| WO | WO 91/02077 | 2/1991 |
| WO | WO 91/15572 | 10/1991 |
| WO | WO 92/01717 | 2/1992 |
| WO | WO 92/08484 | 5/1992 |
| WO | WO 92/08488 | 5/1992 |
| WO | WO 93/14118 | 7/1993 |
| WO | WO 93/17712 | 9/1993 |
| WO | WO 93/18146 | 9/1993 |
| WO | WO 93/18147 | 9/1993 |
| WO | WO 93/21529 | 10/1993 |
| WO | WO 94/03208 | 2/1994 |
| WO | WO 94/03599 | 2/1994 |
| WO | WO 94/04676 | 3/1994 |
| WO | WO 94/11513 | 5/1994 |
| WO | WO 95/04824 | 2/1995 |
| WO | 9506725 | 3/1995 |
| WO | WO 95/24923 | 9/1995 |
| WO | 9601611 | 1/1996 |
| WO | 9602143 | 2/1996 |
| WO | 9610419 | 4/1996 |
| WO | WO 96/10411 | 4/1996 |
| WO | WO 96/31613 | 10/1996 |
| WO | WO 97/06685 | 2/1997 |
| WO | WO 97/06821 | 2/1997 |
| WO | WO 97/06828 | 2/1997 |
| WO | WO 97/10000 | 3/1997 |
| WO | WO 97/10001 | 3/1997 |
| WO | WO 97/10002 | 3/1997 |
| WO | WO 97/26910 | 7/1997 |
| WO | 9735619 | 10/1997 |
| WO | WO 98/23735 | 6/1998 |
| WO | 9942121 | 8/1999 |
| WO | 03005964 | 1/2003 |
| WO | 2004032865 | 4/2004 |
| WO | 2005030136 | 4/2005 |
| WO | 2005092373 | 10/2005 |
| WO | 2009114085 | 9/2009 |
| WO | 2009117116 | 9/2009 |
| WO | 2010060026 | 5/2010 |

OTHER PUBLICATIONS

Anonymous, Novel tumor vaccine pg96-Ig fusion protein in advanced (stage IIIB), relapsed or metastatic (stage IV) non-small cell lung cancer (NSCLC) patients who have ailed first line chemotherapy, ClinicalTrials.gov archive, Dec. 27, 2007; <<http://clinicaltrials.gov/archive/NCT00503568/2007_12_27>>.

Kovalchin, J. T. et al., "Determinants of efficacy of immunotherapy with tumor-derived heat shock protein gp96.", Cancer Immunity, Apr. 27, 2001, vol. 1:7:1-9.

Burton, D.R. et al: "Why do we not have an HIV vaccine and how can we make one?," Nature Medicine, 1998, vol. 4:495-498.

Desrosiers, Ronald C.: "Prospects for an Aids vaccine", Nature Medicine, Mar. 2004, vol. 10, No. 3:221-223.

Girard, M.P. et al: "A review of vaccine research and development: the human immunodeficiency virus (HIV)," Vaccine, 2006, vol. 24:4062-4081.

Matthews, T.J. et al: "Prospects for development of a vaccine against HTLV-III-related disorders," AIDS Research and Human Retroviruses, 1987, vol. 3:197-206.

Strbo, Natasa, et al.: "HLA A2 restricted HIV specific mucosal and systemic immunity induced with secreted heat shock protein gp96-Ig," The FASER Journal, 2008, vol. 22.

U.S. Appl. No. 09/090,754, filed Jun. 4, 1998, Srivastava.

Ausubel et al., ed., 1988, Current Protocols in Molecular Biology (Greene Publish. Assoc. and Wiley Interscience) Chapter 13.

Barrios et al., 1994, "Heat shock proteins as carrier molecules: in vivo helper effect mediated by Escherichia coil GroEL and DnaK proteins requires cross-linking with antigen", Clin. Exp. Immunol. 98:229-233.

Barrios et al., "Mycobacterial heat-shock proteins as carrier molecules. II: the use of the 70-kDa mycobacterial heat-shock protein as carrier for conjugated vaccines that can circumvent the need for adjuvants and Bacillus Calmette Guérin priming", 1992, Eur. J. Immunol. 22:1365-1372.

Barrios et al., 1994, "Specificity of antibodies induced after immunization of mice with the mycobacterial heat shock proteins of 65 kD", Clin. Exp. Immunol. 98:224-228.

Belyaysky et al., 1989, "PCR-based cDNA libraries at the level of a few cells" Nucl. Acids. Res. 17:2919-2932.

Berger et al., 1992, "Guide to molecular cloning techniques", Methods in Enzymol. 152:307-389.

Bernard et al., 1981, "Plasmacytomas with more than one immunoglobulin kappa mRNA: implications for allelic exclusion", Proc. Natl. Acad. Sci. U S A 78(9):5812-5816.

Blachere et al., 1993, "Immunization with GP96 heat shock proteins isolated from tumors or influenza virus infected cells elicits MHC-restricted, antigen-specific cytotoxic T lymphocytes against the corresponding cells/antigens" J. Cell. Biochem. 17D:124.

Blachere et al., 1993, "Heat Shock Protein Vaccines Against Cancer," J. Immunotherapy 14:352-356.

Blachere et al., 1997, "Heat shock protein-peptide complexes, reconstituted in vitro, elicit peptide-specific T lymphocyte response and tumor immunity", J. Exp. Med. 186(8):1315-1322.

Bowen et al., 1996, "Structure and expression of murine CD30 and its role in cytokine production", J. Immunol. 156(2):442-449.

Choulika et al., 1996, "Transfer of a single gene containing long terminal repeats into the genome of mammalain cells by a retroviral vector carrying the cre gene and the loxP site" J. Virol. 70:1792-1798.

Clontech catalog 1997-1998, p. 153.

Craig, 1993, "Chaperones: Helpers Along the Pathways to Protein Folding" Science 260:1902-1904.

Domec et al., 1990, "cDNA library construction form small amounts of unfractionated RNA: association of cDNA synthesis with polymerase chain reaction amplification", Anal. Biochem. 188:422-426.

Ebert, 1987, "Characterization of an immunosuppresive factor derived from colon cancer cells", J. Immunol. 138:2161-2168.

Falk et al., 1990, "Cellular Peptide Composition Governed by Major Histocompatibility Complex Class I Molecules", Nature 348:248-251.

Falk et al., "Allele-specific Motifs Revealed by Sequencing of Self-peptides Eluted from MHC Molecules" 1991, Nature 351:290-296.

Feldweg et al., "Evidence for biochemical heterogeneity of gp96 heat shock protein/tumor rejection antigen" 1993, J. Cell. Biochem. Suppl. 17D:108.

Flynn et al., 1991, "Peptide-binding Specificity of the Molecular Chaperone BiP" Nature 353:726-730.

Flynn et al., 1989, "Peptide binding and release by proteins implicated as catalysts of protein assembly" Science 245:385-390.

Franklin, 1993, "Making vaccines fit the cancer" New Scientist 140:17.

Gething, 1992, "Protein Folding in the Cell" Nature 355:33-45.

Gorman, 1990, "Mammalian Cell Expression", Curr. Opin. Biotechnol. 1:36-47.

(56) References Cited

OTHER PUBLICATIONS

Heike et al., 1994, "Protective Cellular Immunity against a Spontaneous Mammary Carcinoma from *ras* Transgenic Mice", Immunobiology 190:411-423.
Huynh et al., 1984, *DNA Cloning Techniques vol. I: A Practical Approach* (IRL Press, Oxford) pp. 49-78.
Jakob et al., "Small Heat Shock Proteins Are Molecular Chaperones" 1993, J. Biol. Chem. 268:1517-1520.
Jardetzky et al., 1991,"Identification of Self Peptides Bound to Purified HLA-B27" Nature 353:326-329.
Lakey et al., 1987, "Identification of a peptide binding protein that plays a role in antigen presentation" Proc. Natl. Acad. Sci. USA 84:1659-1663.
Lanzavecchia, 1993, "Identifying Strategies for Immune Intervention" Science 260:937-944.
Levinson et al., 1979,"Metal Binding Drugs Induce Synthesis of Four Proteins in Normal Cells" Biol. Trace Element Res. 1:15-23.
Levy, 1991, "ATP is Required for in Vitro Assembly of MHC Class I Antigens but Not for Transfer of Peptides across the ER Membrane" Cell 67:265-274.
Li et al., 1993,"Tumor rejection antigen gp96/grp94 is an ATPase: Implications for protein folding and antigen presentation" EMBO J. 12:3143-3151.
Lindquist et al., 1988,"The heat-shock proteins" Ann. Rev. Genet. 22:631-677.
Luescher et al., 1991, "Specific Binding of Antigenic Peptides to Cell-associated MHC Class I Molecules", Nature 351:72-77.
Lukacs et al., 1993,"Tumor cells transfected with a bacterial heat-shock gene lose tumorigenicity and induce protection against tumors", J. Exp. Med. 178:343-348.
Lussow et al., 1991 "Mycobacterial heat-shock proteins as carrier molecules", Eur. J. Immunol. 21:2297-2302.
Madden et al., 1991 "The Structure of HLA-B27 Reveals Nonamer Self-peptides Bound in an Extended Conformation", Nature 353:321-325.
Maki et al., 1993,"Mapping of the Genes for Human Endoplasmic Reticular Heat Shock Protein gp96/grp94" Somatic Cell Mol, Genetics 19:73-81.
Maki et al., 1990,"Human homologue of murine tumor rejection antigen gp96: 5'-Regulatory and coding regions and relationship to stress-induced proteins" Proc. Natl. Acad. Sci. USA 87:5658-5663.
Makrides, 1996, "Strategies for achieving high level expression of genes in *Escherichia coli*" Microbiol. Rev. 60:512-538.
McCall et al., 1989 "Biotherapy: A New Dimension in Cancer Treatment", Biotechnology 7:231-240.
Menoret et al., 1995, "Co-segregation of tumor immunogenicity with expression of inducible but not constitutive hsp70 in rat colon carcinomas", J. Immunol. 155(2):740-747.
Mizoguchi et al., 1982, "Alterations in signal transduction molecules in T lymphocytes from Tumor-bearing mice",Science 258:1795-1798.
Munro and Pelham, 1987, "A C-terminal signal prevents secretion of luminal ER proteins", Cell 48:899-907.
Palladino et al., 1987 "Expression of shared tumor-specific antigen by two chemically induced BALB/c sarcomas", Cancer Res. 47:5074-5079.
Pidoux and Armstrong, 1992, "Analysis of the BiP gene and identification of an ER retention signal in Schizosaccharomyces pombe", EMBO J. 11:1583-1591.
Prehn et al., 1957,"Immunity to methylcholanthrene-induced sarcomas" J. Cancer Inst. 18:769-778.
Rothman, 1989 "Polypeptide Chain Binding Proteins: Catalysts of Protein Folding and Related Processes in Cells", Cell 59:591-601.
Rotzschke et al., 1990, "Isolation and Analysis of Naturally Processed Viral Peptides as Recognized by Cytotoxic T cells" Nature 348:248-251.
Rudensky et al.,1991, "Sequence analysis of peptides bound to MHC class II molecules", Nature 353:622-627.
Salk et al., 1993, "A Strategy for Prophylactic Vaccination Against HIV" Science 260:1270-1272.
Sambrook et al., in *Molecular Cloning: A Laboratory Manual*, 2$^{nd}$ Ed., Chapter 8, 1989.
Schumacher et al., 1991 "Peptide Selection by MHC Class I Molecules", Nature 350:703-706.
Srivastava et al., 1991, "Stress-induced proteins in immune response to cancer", Curr. Top. Microbiol. Immunol. 167:109-123.
Srivastava et al., 1994"Heat shock proteins transfer peptides during antigen processing and CTL priming", Immunogenetics 39:93-98.
Srivastava et al., 1989,"Identification of a Human Homologue of the Murine Tumor Rejection Antigen GP96," Cancer Res. 49:1341-1343.
Srivastava et al., 1993,"Peptide-Binding Heat Shock Proteins in the Endoplasmic Reticulum: Role in Immune Response to Cancer and in Antigen Presentation" Adv. Cancer Res. 62:153-177.
Srivastava et al., 1987 "5'-Structural analysis of genes encoding polymorphic antigens of chemically induced tumors", Proc. Natl. Acad. Sci, USA 84:3807-3811.
Srivastava et al., 1988, "Chromosonal Assignment of the Gene Encoding the Mouse Tumor Rejection Antigen gp96" Immunogenetics 28:205-207.
Srivastava et al., 1986 "Tumor rejection antigens of chemically induced sarcomas of inbred mice", Proc. Natl. Acad. Sci. USA 83:3407-3411.
Srivastava et al., 1984 "The Serologically Unique Cell Surface Antigen of Zajdela Ascitic Hepatoma is also its Tumor-Associated Transplantation Antigen", Int. J. Cancer 33:417-422.
Srivastava, 1991,"Protein Tumor Antigens", Curr. Opin. Immunol. 3:654-658.
Srivastava et al., 1993,"Evidence for peptide-chaperoning by the endoplasmic reticular heat shock protein GP96: Implications for vaccination against cancer and infectious diseases" J. Cell. Biochem. Supp. 17D:94 (Abstract NZ 014).
Srivastava et al., 1988,"Individually distinct transplantation antigens of chemically induced mouse tumors" Immunol. Today 9:78-83.
Subbarao et al., 1992,"A General Overview of Viral Vaccine Development," Genetically Engineered Vaccines 327:51-57.
Suto et al., 1995,"A Mechanism for the Specific Immunogenicity of Heat Shock Protein-Chaperoned Peptides", Science 269:1585-1588.
Udono et al., 1994, "Cellular requirements for tumor-specific immunity elicited by heat shock proteins:tumor rejection antigen gp96 primes CD8+ T cells in vivo", Proc. Natl. Acad. Sci. USA 91:3077-3081.
Udono, 1993,"Heat shock proteins HSP70, HSP90 and GP96 elicit tumor specific immunity to the tumors from which they are isolated" J. Cell. Biochem. Suppl. 17D:113 (Abstract NZ225).
Udono et al., 1993, "Heat Shock Protein 70-associated Peptides Elicit Specific Cancer Immunity" J. Exp. Med. 178:1391-1396.
Udono et al., 1993 "Comparison of Tumor-Specific Immunogenicities of Stress-Induced Proteins gp96, hsp90, and hsp70", J. Immunol. 152:5398-5403.
Ullrich et al., 1986,"A mouse tumor-specific transplantation antigen is a heat shock-related protein" Proc. Natl. Acad. Sci. USA 83:3121-3125.
Van den Enyde et al., 1991, "The gene coding for a major tumor rejection antigen of tumor P815 is identical to the normal gene of syngeneic DBA/2 mice", J. Exp. Med. 173:1373-1384.
Vanbuskirk et al., 1989, "Peptide binding protein having a role in antigen presentation is a member of the hsp70 heat shock family", J. Exp. Med. 170:1799-1809.
Viitanen et al., 1992, "Mammalian mitochondrial chaperonin 60 functions as a single toroidal ring", J. Biol. Chem. 267:695-698.
von Heijne,1985, "Signal sequences. The limits of variation", J. Mol. Biol. 184(1):99-105.
Welch et al., 1985, "Rapid Purification of Mammalian 70,000-Dalton Stress Proteins: Affinity of the Proteins for Nucleotides" Mol. Cell. Biol. 5:1229-1237.
Welch, 1993,"How Cells Respond to Stress" Scientific American pp. 56-64.
Welch et al., 1985, "Morphological study of the mammalian stress response: characterization of changes in cytoplasmic organelles, cytoskeleton, nucleoli, and appearance of intranuclear actin filaments in rat fibroblast after heat shock treatment", J. Cell. Biol. 101:1198-1211.

(56) References Cited

OTHER PUBLICATIONS

Welch et al., 1982, "Purification of the Major Mammalian Heat Shock Proteins" J. Biol. Chem. 357:14949-14959.
Yamazaki et al., 1997, "gp96 engineered for secretion of tumor peptides and for vaccination against cancer", J. Allergy Clin. Immunol. 95:845 (abst. 187).
Yamazaki et al., "Cutting edge: tumor secreted heat shock-fusion protein elicits CD8 cells for rejection", J Immunol. Nov. 15, 1999;163(10)5178-82.
Young, 1990,"Stress Proteins and Immunology" Annu. Rev. Immunol. 8:401-420.
Wang et al., 2001, "Characterization of heat shock protein 110 and glucose-regulated protein 170 as cancer vaccines and the effect of fever-range hyperthermia on vaccine activity" J. Immunol. 166(1):490-497.
Zugel U et al., 2001, "gp96-peptide vaccination of mice against intracellular bacteria" Infect. Immun. 69(6):4164-4167.
*Healthcare Professionals—Results of Past Trials*, Retrieved from Website of Antigenics Inc. on the Internet at: <URL: www.antigenics.com/p_healthcare03.html> on Oct. 19, 2001.
Ausubel et al., ed., 1999, *Short Protocols in Molecular Biology* (4th Edition, John Wiley & Sons, Inc., New York) Unit 10.11, pp. 10-86 to 10-88.
Evans and Kaye, 1999, "Vaccine therapy for cancer—fact or fiction?" Q. J. Med. 92:299-307.
*The American Heritage Dictionary*, 1982 (2nd College Edition, Houghton Mifflin Company) pp. 135 and 1173.
Janetzki et al., 2000, "Immunization of cancer patients with autologous cancer-derived heat shock protein gp96 preparations: a pilot study" Int. J. Cancer 88(2):232-238.
Tamura et al., 1997, "Immunotherapy of tumors with autologous tumor-derived heat shock protein preparations" Science 278(5335):117-120.
Hickey WF, 2001, "Basic principles of immunological surveillance of the normal central nervous system." Glia.36:118-24.
Perrin et al., 1999, "Astrocytoma infiltrating lymphocytes include major T cell clonal expansions confined to the CD8 subset." Int Immunol. 11(8):1337-49.
Roy et al., 2000, "IL-12 treatment of endogenously arising murine brain tumors." J Immunol.165(12):7293-9.
Clontech catalog 1995-1996, Table of Contents, and pp. 137-138.
Sigma Life Science Research Immunochemicals 1998 catalog and price list @ 1997, Table of Contents, and pp. 144-146.
Yamazaki et al., "Effective therapeutic anti-tumor immunity generated by tumors secreting gp96-Ig in syngeneic immunocompetent mice", 93rd Annual Meeting of the American Association of Cancer Research, Mar. 2002, Abstract #4821.
Colombo et al., "Direct in vivo DC targeting by cellular vaccines engineered to express OX-40L/GM-CSF or soluble HSP70", 93rd Annual Meeting of the American Association of Cancer Research, Mar. 2002, Abstract #3370.
Feldweg et al., 1995, "Molecular heterogeneity of tumor rejection antigen/heat shock protein GP96", Intl. J. Cancer 63:310-314.
Meerovitch et al., 1998, "Proparathyroid hormone-related protein is associated with the chaperone protein BiP and undergoes proteasome-mediated degradation", J. Biol. Chem. 273:21025-21030.
Dai, J. et al: "Cell surface expression of heat shock protein gp96 enhances cross-presentation of cellular antigens and the generation of tumor-specific T cell memory," Cancer Immunity, 2003, vol. 3:1.
Inoue, S. et al: "Inhibitory effects of B cells on antitumor immunity," Cancer Research, 2006, vol. 66 (15).
Zheng, H. et al: "Cell surface targeting of heat shock protein gp96 induces dendritic cell maturation and antitumor immunity," The Journal of Immunology, 2001, pp. 6731-6735.
Multhoff, G. et al: "Heat shock protein 72 on tumor cells," The Journal of Immunology, 1997, pp. 4341-4350.
Heike, M. et al: "Heat shock protein-peptide complexes for use in vaccines, " Journal of Leukocyte Biology, 1995, vol. 60:153-158.
Oizumi, S. et al: "Molecular and cellular requirements for enhanced antigen cross-presentation to CD8 cytotoxic T lymphocytes", The Journal of Immunology, 2007, vol. 179:2310-2317.
Strbo, N. et al: "Heat shock fusion protein gp96-Ig mediates strong CD8 CTL expansion in vivo," American Journal of Reproductive Immunology, 2002, vol. 48:220-225.
U.S. Appl. No. 13/112,341 (Podack) filed on May 20, 2011 (not yet published), "Cancer treatment".
U.S. Appl. No. 13/129,920 (Podack) filed on May 18, 2011 (not yet published) , "HIV/SIV Vaccines for the generation of mucosal and systemic immunity".
Strbo, N. and Podack, ER.: "Secreted heat shock protein gp96-Ig: an innovative vaccine approach," American Journal of Reproductive Immunology, 2008, vol. 59:407-416.
Oizumi, S. et al: "Surmounting tumor-induced immune suppression by frequent vaccination or immunization in the absence of B cells," J. Immunotherapy, 2008, vol. 31:394-401.
Li, J. et al: "Heat shock protein 70 fused to or complexed with hantavirus nucleocapsid protein significantly enhances specific humoral and cellular immune responses in C57BL/6 mice," Vaccine, 2008, vol. 26:3175-3187.
Segal, B.H. et al: "Heat shock proteins as vaccine adjuvants in infections and cancer," Drug Discovery Today, 2006, vol. 11:534-540.
Gullo, C. and Teoh, G.: "Heat shock proteins: to present or not, that is the question," Immunology Letters, 2004, vol. 94:1-10.
Strbo, N. et al: "Secreted gp-96-Ig mediates CD8 and NK cell expansion," FASEB Journal, vol. 16, No. 4, 2002, XP008143902 (Abstract).
Yamazaki, K. et al: "Induction of tumor immunity by gp96 secreted from engineered tumor cells," 2000, Lung Cancer, vol. 29, No. 1, XP027413932 (Abstract).
Strbo, N. et al: "OA05-04. Gp96-Ig-SIV vaccines induce predominant immune responses at mucosal sites," Retrovirology, 2009, vol. 6:1.
Strbo, N. et al: "Cell-secreted Gp96-Ig-peptide complexes induce lamina propria and intraepithelial CD8+ cytotoxic T lymphocytes in the intestinal mucosa, " Immunology, 2010, vol. 3, No. 2 :182-192.
Strbo, N. et al: "SIV-gp96-Ig vaccine induces high levels of adaptive mucosal CD8 effector cells in rhesus macaques," Journal of Medical Primatology, 2010, vol. 39, X008143996 (Abstract).
Strbo, N. et al: "Gp96SIV Ig immunization induces potent polyepitope specific, multifunctional memory responses in rectal and vaginal mucosa," Vaccine, 2011, vol. 29, No. 26:2619-2626.
Strbo, N. et al:"Heat shock fusion protein gp96-Ig mediates strong CD8 CTL Expansion in vivo," American Journal of Reproductive Immunology, 2002, vol. 48:220-225.
Wheeler, CM.: "Preventive vaccines for cervical cancer," Salud Publica Mex, 1997, vol. 39:283-287.
Arnold et al. "Inflences of transporter associated with antigen processing (TAP) on the repertoire of peptides associated with the endoplasmic reticulum-resident stress protein gp96" J. Exp. Med. 186:461-466 (1997).
Breloer et al. "Isolation of processed, H-2K-binding ovalbumin-derived peptides associated with the stress proteins HSP70 and GP96" Eur. J. Immunol. 28:1016-1021 (1998).
Lukacs et al. "In vivo gene therapy of malignant tumours with heat shock protein-65 gene" Gene Ther. 4:346-350 (1997).
Nicchitta "Biochemical, cell biological and immunological issues surrounding the endoplasmic reticulum chaperone GRP94/gp96" Curr. Op. Immunol. 10:103-109 (1998).
Srivastava et al. "Heat shock proteins transfer peptides during antigen processing and CTL priming" Immun. 39:93-98 (1994).
Partial European Search Report for European Appln. No. 07007299.6 dated Jul. 25, 2007.

\* cited by examiner

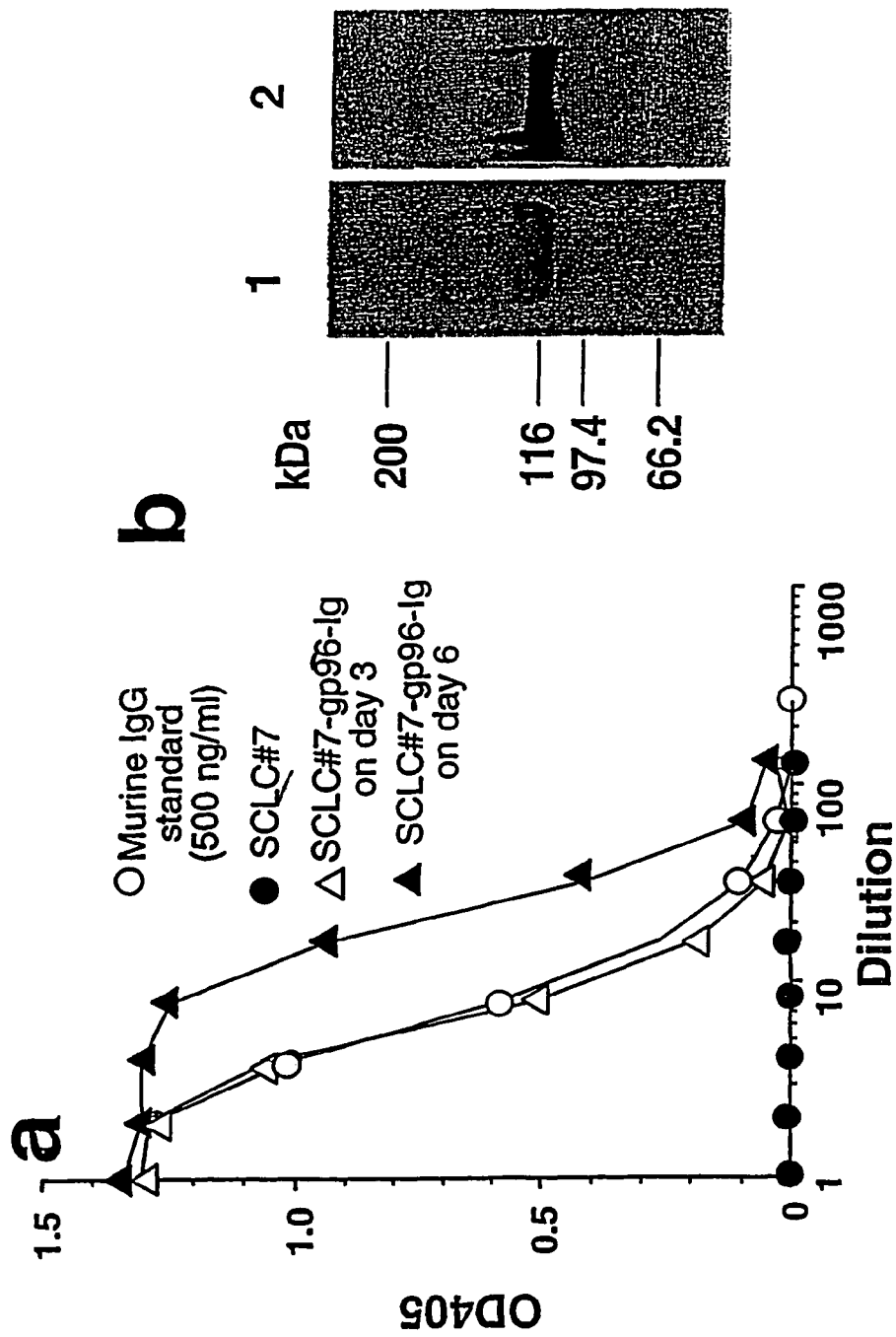
FIGS. 1A-B

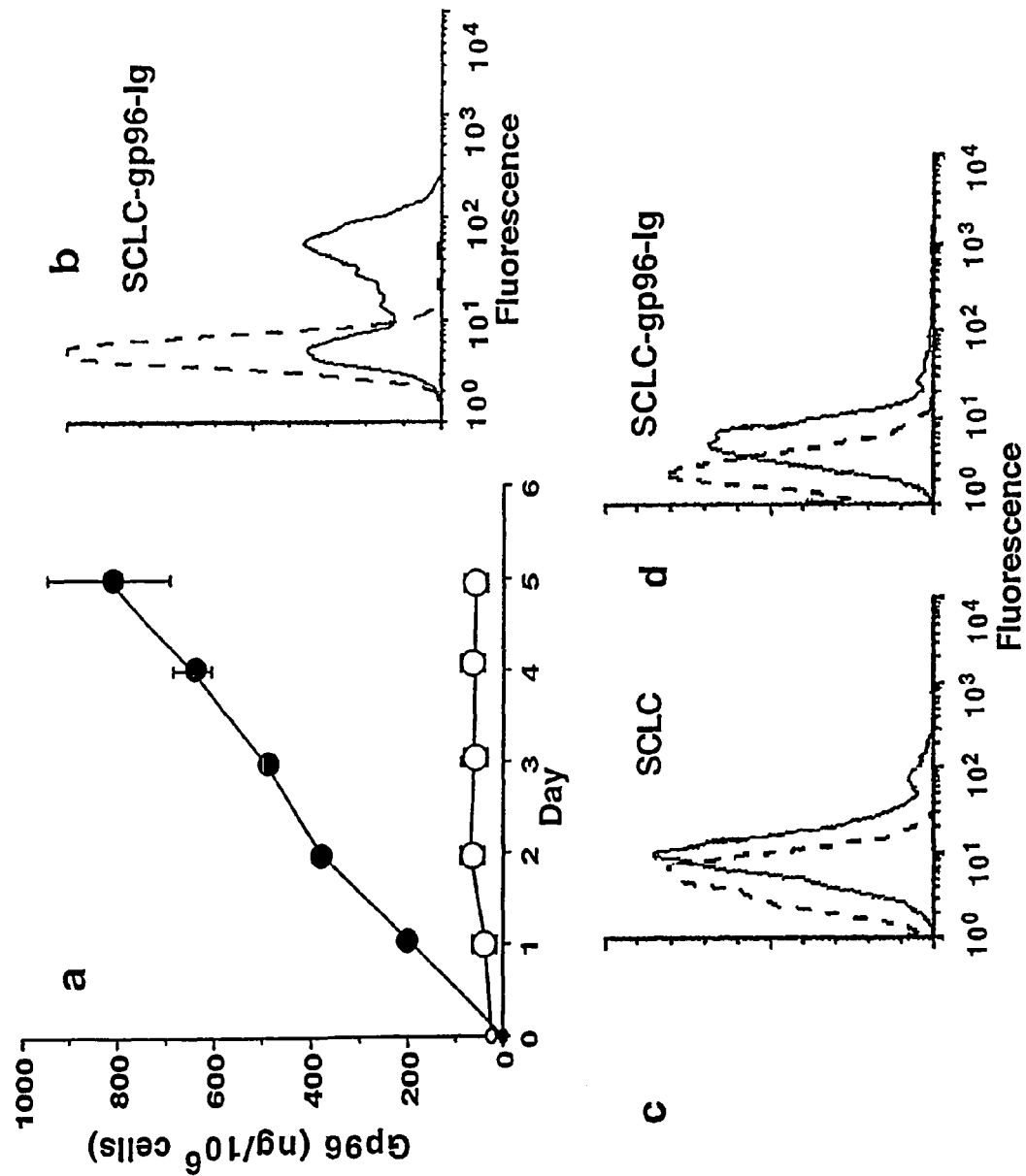
FIGS. 2A-D

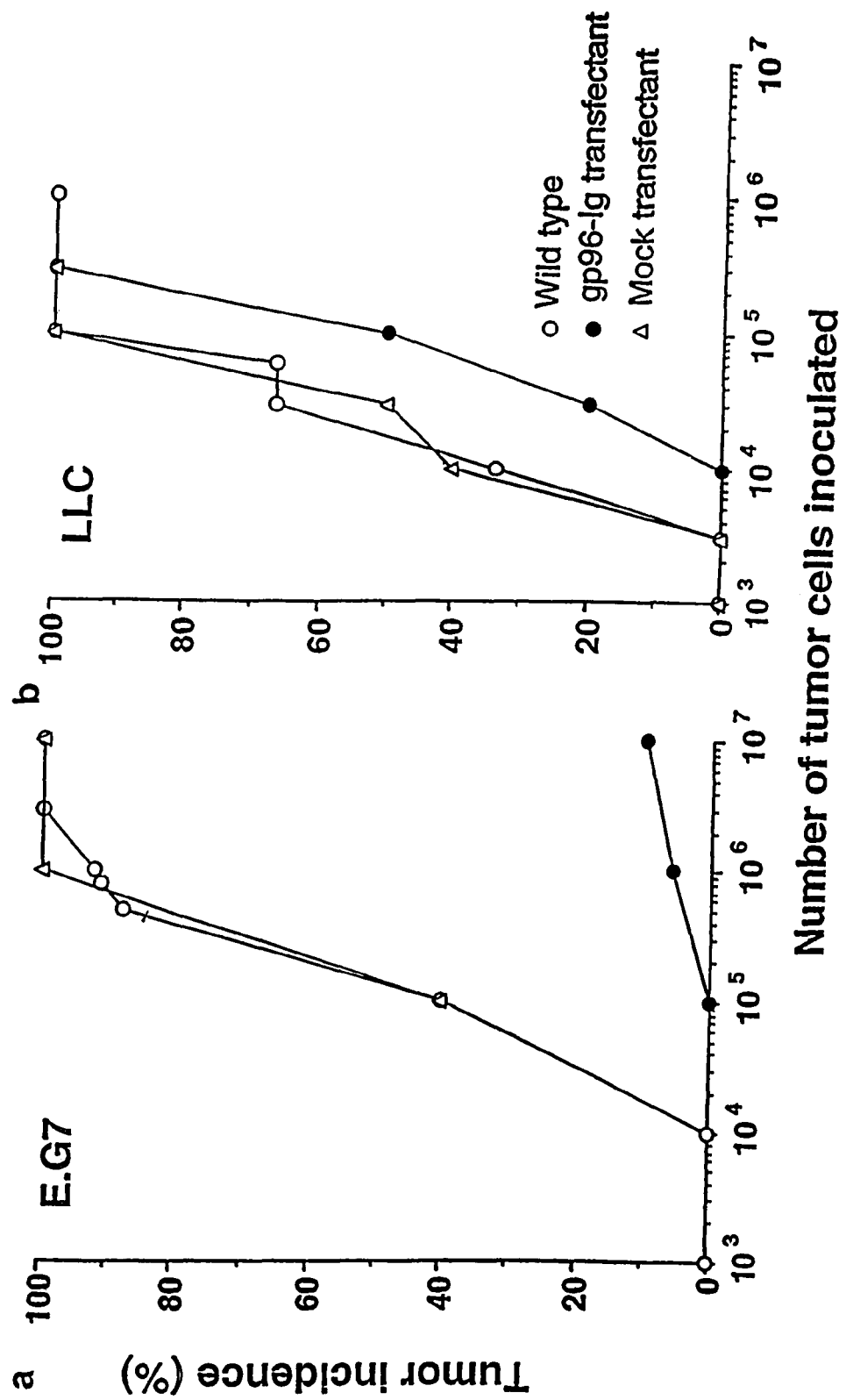
FIGS. 3A-B

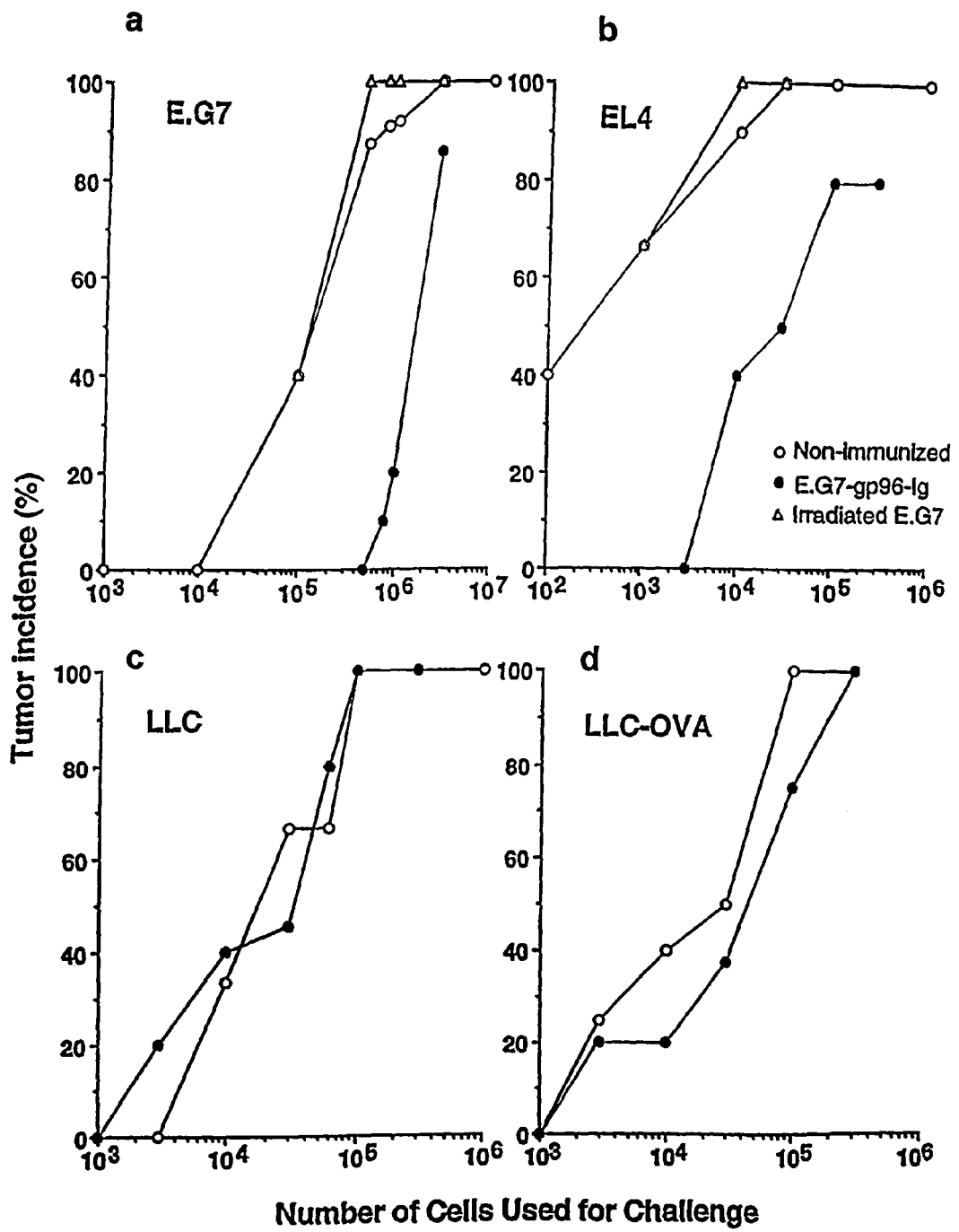
FIGS. 4A-D

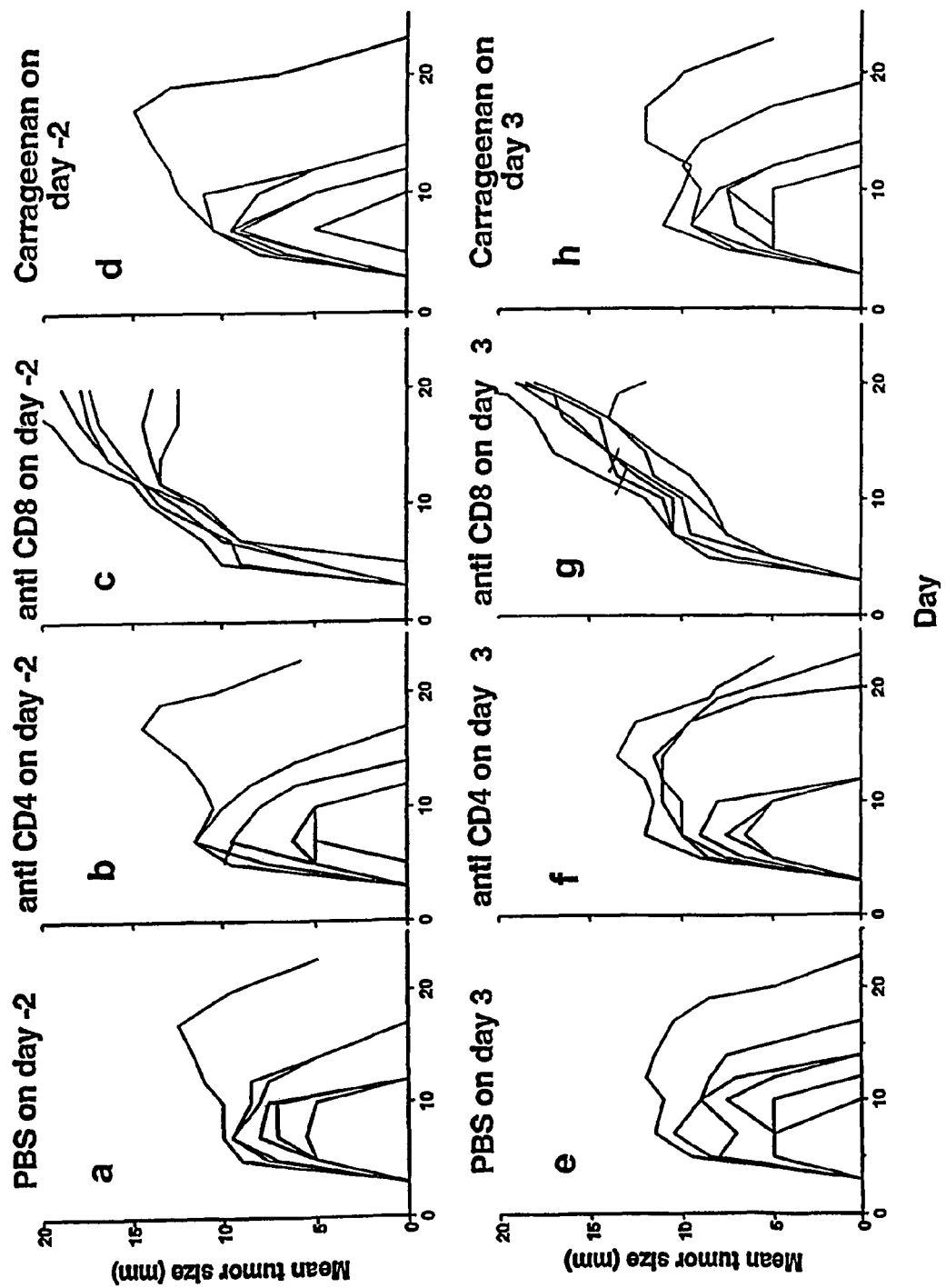
FIGS. 5A-H

RECOMBINANT CANCER CELL SECRETING MODIFIED HEAT SHOCK PROTEIN-ANTIGENIC PEPTIDE COMPLEX

This application is a division of application Ser. No. 09/253,439, filed Feb. 19, 1999, now abandoned; which claims the benefit of Application No. 60/075,358, filed Feb. 20, 1998; the contents of which are incorporated by reference in their entirety.

STATEMENT REGARDING FEDERALLY SPONSORED RESEARCH OR DEVELOPMENT

This invention was made with government support under grant number CA57904 awarded by the National Institutes of Health. The government has certain rights in the invention.

1. INTRODUCTION

The present invention relates to methods for preparing immunogenic material that is useful as a vaccine for the prevention and/or treatment of cancer or infectious diseases. The vaccine is comprised of noncovalent complexes of modified heat shock proteins (hsp), including, but not limited to, hsp70, hsp90, gp96, and protein disulfide isomerase, and antigenic peptides. The vaccine is capable of eliciting or augmenting a subject's immune response against particular types of cancer or infected cells.

2. BACKGROUND OF THE INVENTION

2.1. Pathobiology of Cancer

Cancer is characterized primarily by an increase in the number of abnormal cells derived from a given normal tissue. The disease process also involves invasion of adjacent tissues by these abnormal cells, and spread of these abnormal cells to regional lymph nodes and to distant sites (metastasis) via the circulatory system. Clinical data and molecular biologic studies indicate that cancer is a multistep process that begins with minor preneoplastic changes, which may under certain conditions progress to neoplasia.

Pre-malignant abnormal cell growth is exemplified by hyperplasia, metaplasia, or most particularly, dysplasia (for review of such abnormal growth conditions, see Robbins and Angell, 1976, Basic Pathology, 2d Ed., W.B. Saunders Co., Philadelphia, pp. 68-79.) Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

The neoplastic lesion may evolve clonally and develop an increasing capacity for invasion, growth, metastasis, and heterogeneity, especially under conditions in which the neoplastic cells escape the host's immune surveillance (Roitt, I., Brostoff, J. and Male, D., 1993, Immunology, 3rd ed., Mosby, St. Louis, pps. 17.1-17.12).

2.2. Vaccination

Vaccination has eradicated certain diseases such as polio, tetanus, chicken pox, measles, etc. in many countries of the world. This approach has exploited the ability of the immune system to prevent infectious diseases. Such vaccination with non-live materials such as proteins generally leads to an antibody response or CD4+ helper T cell response (Raychaudhuri & Morrow, 1993, Immunology Today, 14:344-348). On the other hand, vaccination or infection with live materials such as live cells or infectious viruses generally leads to a CD8+ cytotoxic T-lymphocyte (CTL) response. A CTL response is crucial for protection against cancers, infectious viruses and bacteria. This poses a practical problem, for, the only way to achieve a CTL response is to use live agents which are themselves pathogenic. The problem is generally circumvented by using attenuated viral and bacterial strains, or by killing whole cells which can be used for vaccination. These strategies have worked well but the use of attenuated strains always carries the risk that the attenuated agent may recombine genetically with host DNA and turn into a virulent strain. Thus, there is need for methods which can lead to CD8+ CTL response by vaccination with non-live materials such as proteins in a specific manner.

The era of tumor immunology began with experiments by Prehn and Main, who showed that antigens on the methylcholanthrene (MCA)-induced sarcomas were tumor specific in that transplantation assays could not detect these antigens in normal tissue of the mice (Prehn et al., 1957, J. Natl. Cancer Inst. 18:769-778). This notion was confirmed by further experiments demonstrating that tumor specific resistance against MCA-induced tumors can be elicited in the mouse in which the tumor originated (Klein et al., 1960, Cancer Res. 20:1561-1572).

In subsequent studies, tumor specific antigens were also found on tumors induced with other chemical or physical carcinogens or on spontaneous tumors (Kripke, 1974, J. Natl. Cancer Inst. 53:1333-1336; Vaage, 1968, Cancer Res. 28:2477-2483; Carswell et al., 1970, J. Natl. Cancer Inst. 44:1281-1288). Since these studies used protective immunity against the growth of transplanted tumors as the criterion for tumor specific antigens, these antigens are also commonly referred to as "tumor specific transplantation antigens" or "tumor specific rejection antigens." Several factors can greatly influence the immunogenicity of the tumor, including, for example, the specific type of carcinogen involved, immunocompetence of the host and latency period (Old et al., 1962, Ann. N.Y. Acad. Sci. 101:80-106; Bartlett, 1972, J. Natl. Cancer Inst. 49:493-504).

Most, if not all, carcinogens are mutagens which may cause mutation, leading to the expression of tumor specific antigens (Ames, 197.9, Science 204:587-593; Weisburger et al., 1981, Science 214:401-407). Some carcinogens are immunosuppressive (Malmgren et al., 1952, Proc. Soc. Exp. Biol. Med. 79:484-488). Experimental evidence suggests that there is a constant inverse correlation between immunogenicity of a tumor and latency period (time between exposure to carcinogen and tumor appearance) (Old et al., 1962, Ann. N.Y. Acad. Sci. 101:80-106; and Bartlett, 1972, J. Natl. Cancer Inst. 49:493-504). Other studies have revealed the existence of tumor specific antigens that do not lead to rejection, but, nevertheless, can potentially stimulate specific immune

2.3. Heat Shock Proteins

Heat shock proteins (hsps) are also referred to interchangeably as stress proteins. The first stress proteins to be identified were proteins synthesized by a cell in response to heat shock. To date, three major families of hsp have been identified based on molecular weight. The families have been called hsp60, hsp70 and hsp90 where the numbers reflect the approximate molecular weight of the stress proteins in kilodaltons. Many members of these families were found subsequently to be induced in response to other stressful stimuli including nutrient deprivation, metabolic disruption, oxygen radicals, and infection with intracellular pathogens. (See Welch, May 1993, Scientific American 56-64; Young, 1990, Annu. Rev. Immunol. 8:401-420; Craig, 1993, Science 260: 1902-1903; Gething et al., 1992, Nature 355:33-45; and Lindquist et al., 1988, Annu. Rev. Genetics 22:631-677).

The major hsps can accumulate to very high levels in stressed cells, but they occur at low to moderate levels in cells that have not been stressed. For example, the highly inducible mammalian hsp70 is hardly detectable at normal temperatures but becomes one of the most actively synthesized proteins in the cell upon heat shock (Welch et al., 1985, J. Cell. Biol. 101:1198-1211). In contrast, hsp90 and hsp60 proteins are abundant at normal temperatures in most, but not all, mammalian cells and are further induced by heat (Lai et al., 1984, Mol. Cell. Biol. 4:2802-2810; van Bergen en Henegouwen et al., 1987, Genes Dev. 1:525-531).

Heat shock proteins are among the most highly conserved proteins in existence. For example, DnaK, the hsp70 from *E. coli* has about 50% amino acid sequence identity with hsp70 proteins from excoriates (Bardwell et al., 1984, Proc. Natl. Acad. Sci. 81:848-852). The hsp60 and hsp90 families also show similarly high levels of intra families conservation (Hickey et al., 1989, Mol. Cell. Biol. 9:2615-2626; Jindal, 1989, Mol. Cell. Biol. 9:2279-2283). In addition, it has been discovered that the hsp60, hsp70 and hsp90 families are composed of proteins that are related to the stress proteins in sequence, for example, having greater than 35% amino acid identity, but whose expression levels are not altered by stress.

Studies on the cellular response to heat shock and other physiological stresses revealed that the hsps are involved not only in cellular protection against these adverse conditions, but also in essential biochemical and immunological processes in unstressed cells. The hsps accomplish different kinds of chaperoning functions. For example, hsp70, located in the cell cytoplasm, nucleus, mitochondria, or endoplasmic reticulum, (Lindquist, S. et al., 1988, Ann. Rev. Genetics 22:631-677) are involved in the presentation of antigens to the cells of the immune system, and are also involved in the transfer, folding and assembly of proteins in normal cells.

A number of proteins thought to be involved in chaperoning functions are residents of the endoplasmic reticulum (ER) lumen and include, for example, protein disulfide isomerase (PDI; Gething et al., 1992, Nature 355:33-45), Grp94 or ERp99 (Sorger & Pelham, 1987, J. Mol. Biol. 194:(2) 341-4) which is related to hsp90, and Grp78 or BiP, which is related to hsp70 (Munro et al., 1986, Cell 46:291-300; Haas & Webl, 1983, Nature 306:387-389). These proteins are known to bind a variety of mutant, unfolded, incompletely glycosylated proteins (Machamer et al., 1990, J. Biol. Chem. 65:6879-6883; Gething et al., 1986, Cell 46:939-950). The localization of these hsps in the ER is mediated by a carboxyl terminal tetrapeptide which is necessary for retention in the ER (Munro & Pelham, 1987, Cell, 48:899-907).

Generally, heat shock proteins are capable of binding proteins or peptides, and releasing the bound proteins or peptides in the presence of adenosine triphosphate (ATP). It is believed that ATP hydrolysis occurs during the participation of hsps in course of protein assembly (Flynn et al., 1989, Science, 245: 385-390).

2.4. Immunogenicities of Heat Shock/Stress Proteins hsp70, hsp90 and gp96

Srivastava et al. demonstrated immune response to methylcholanthrene-induced sarcomas of inbred mice (1988, Immunol. Today 9:78-83). In these studies, it was found that the molecules responsible for the individually distinct immunogenicity of these tumors were identified as cell-surface glycoproteins of 96 kDa (gp96) and intracellular proteins of 84 to 86 kDa (Srivastava, P. K. et al., 1986, Proc. Natl. Acad. Sci. USA 83:3407-3411; Ullrich, S. J. et al., 1986, Proc. Natl. Acad. Sci. USA 83:3121-3125). Immunization of mice with gp96 or p84/86 isolated from a particular tumor rendered the mice immune to that particular tumor, but not to antigenically distinct tumors. Isolation and characterization of genes encoding gp96 and p84/86 revealed significant homology between them, and showed that gp96 and p84/86 were, respectively, the endoplasmic reticular and cytosolic counterparts of the same heat shock proteins (Srivastava, P. K. et al., 1988, Immunogenetics 28:205-207; Srivastava, P. K. et al., 1991, Curr. Top. Microbiol. Immunol. 167:109-123). Further, hsp70 was shown to elicit immunity to the tumor from which it was isolated but not to antigenically distinct tumors. However, hsp70 depleted of peptides was found to lose its immunogenic activity (Udono, M., and Srivastava, P. K., 1993, J. Exp. Med. 178:1391-1396). These observations suggested that the heat shock proteins are not immunogenic per se, but form noncovalent complexes with antigenic peptides, and the complexes can elicit specific immunity to the antigenic peptides (Srivastava, P. K., 1993, Adv. Cancer Res. 62:153-177; Udono, H. et al., 1994, J. Immunol., 152:5398-5403; Suto, R. et al., 1995, Science, 269:1585-1588).

The use of noncovalent complexes of stress protein and peptide, purified from cancer cells, for the treatment and prevention of cancer has been described in PCT publications WO 96/10411, dated Apr. 11, 1996, and WO 97/10001, dated Mar. 20, 1997 (see also copending U.S. patent application Ser. No. 08/796,319 filed Feb. 7, 1997 by Srivastava and Chandawarkar and Ser. No. 08/796,316 filed Feb. 7, 1997 by Srivastava, each of which is incorporated by reference herein in its entirety).

Stress protein-peptide complexes can also be isolated from pathogen-infected cells and used for the treatment and prevention of infection caused by the pathogen, such as viruses, and other intracellular pathogens, including bacteria, protozoa, fungi and parasites. See PCT publication WO 95/24923, dated Sep. 21, 1995.

Immunogenic stress protein-peptide complexes can also be prepared by in vitro complexing of stress protein and antigenic peptides, and the uses of such complexes for the treatment and prevention of cancer and infectious diseases has been described in PCT publication WO 97/10000, dated Mar. 20, 1997. The use of heat shock protein in combination with a defined antigen for the treatment of cancer and infectious diseases have also been described in PCT publication WO97/06821 dated Feb. 27, 1997.

The use of stress protein-peptide complexes for sensitizing antigen presenting cells in vitro for use in adoptive immunotherapy is described in PCT publication WO 97/10002, dated Mar. 20, 1997.

The administration of expressible polynucleotides encoding eukaryotic heat shock proteins to mammalian cells for stimulating an immune response, and for treatment of infectious diseases and cancer has been described in PCT publications, WO 97/06685 and WO 97/06828, both dated Feb. 27, 1997.

The purification of stress protein-peptide complexes from cell lysate has been described previously; see for example, PCT Publication WO 95/24923, dated Sep. 21, 1995.

For the purpose of preparing a vaccine against cancer, the amount of immunogenic material obtainable for use is directly related to the amount of starting cancer cells. Since only a small number of cancer cells can be obtained from a subject, especially if the cancer is at an early stage, the supply of cancer cells for producing the hsp-peptide complex is often very limited. For commercial production of a vaccine or therapeutic agent, a constant supply of large amounts of hsp-peptide complexes is advantageous. Thus, there is a need for a dependable source of hsp-peptide complexes. The methods of the present invention can be used to provide therapeutic hsp-peptide complexes in a convenient and rapid manner even when only a very small amount of tissue is available from a patient.

3. SUMMARY OF THE INVENTION

The present invention relates to methods for preparing an immunogenic composition for use in the prevention and treatment of cancer or infectious diseases.

The immunogenic compositions prepared by the methods of the invention comprise noncovalently associated molecular complexes of a modified heat shock protein (hsp) and an antigenic (or immunogenic) peptide. The modified heat shock proteins of the invention is secreted by a cell in which it is expressed; lacks an endoplasmic reticulum retention sequence present in the unmodified heat shock protein; and comprises a peptide tag. For a hsp that naturally reside in the cytoplasm, it is modified so that it is secreted by a cell in which it is expressed; comprises a peptide tag; and comprises a leader peptide not present in the unmodified heat shock protein. The modification does not interfere or impair the non-covalent binding of peptides by a modified heat shock protein, and the ability of the non-covalent complexes to participate in antigen presentation. When the modified hsps are expressed in recombinant cells, they are secreted and can be purified by the peptide tag using affinity chromatography.

In one embodiment, the invention provides nucleic acids comprising nucleotide sequences encoding modified hsps ("modified hsp gene sequences"), and cloning vectors, expression vectors, and host cells containing such nucleic acids. Generally, the methods of the invention comprise constructing a nucleotide sequence encoding a modified heat shock protein, cloning the modified hsp gene sequence into an expression vector, introducing the expression gene construct into host cells, culturing the host cells so that the modified hsp is expressed, and purifying the modified hsp and/or the modified hsp-peptide complexes.

The cDNA or genomic DNA encoding a heat shock protein can be obtained and modified by conventional DNA cloning and mutagenesis methods, by DNA amplification methods, or by synthetic methods. In general, the sequence encoding the hsp is inserted into a cloning vector for genetic modification and replication purposes prior to expression. The modified hsp gene sequences are inserted into an expression vector or intrachromosomally integrated, operatively linked to regulatory element(s) such as a promoter, for purposes of expressing the encoded modified hsps in suitable host cells in vitro and in vivo. The modified hsp gene sequences are introduced into host cells where they are expressed by the host cells, thereby producing intracellularly noncovalent complexes of modified hsps and peptides (including those peptides specifically encoded by the cancer cells or the pathogenic infectious agent).

Accordingly, the invention provides methods for producing and purifying immunogenic non-covalent complexes of modified hsps and antigenic peptides in antigenic cells comprising introducing a modified hsp gene sequence into the antigenic cells, culturing the recombinant antigenic cells to allow expression of the modified hsp gene sequence, and recovering and purifying the modified hsp-antigenic peptide complexes that is secreted from the recombinant antigenic cells from the cell culture supernatant. The antigenic peptides of the complexes are representative of antigenic peptides found in antigenic cells, such as cancer cells or pathogen-infected cells. Such recombinant antigenic cells are useful as a vaccine for therapeutic and prophylactic uses. The recombinant host cells can be cultured in batch or continuously on a large scale for production of large amounts of the immunogenic complexes. The host cells containing the modified hsp sequences can be stored for future use (e.g., by lyophilization or freezing).

In another embodiment, the invention provides methods for producing and purifying modified hsps in cells comprising introducing a modified hsp gene sequence into the cells, culturing the recombinant cells to allow expression of the modified hsp gene sequence, and recovering and purifying the modified hsp that is secreted from the recombinant cells from the cell culture supernatant. Preferably, purification of the modified hsps are facilitated by the peptide tag and affinity chromatography. The invention further provides that the purified modified hsps can be loaded in vitro with antigenic peptides to form immunogenic non-covalent complexes for therapeutic and prophylactic uses.

In yet another embodiment, the invention provides methods for producing and purifying immunogenic non-covalent complexes comprising co-expressing a modified hsp gene sequence and a nucleotide sequence encoding an antigenic peptide in recombinant cells, and recovering and purifying the modified hsp-antigenic peptide complexes that is secreted from the recombinant cells from the cell culture supernatant. These recombinant cells can also be used as a vaccine for therapeutic and prophylactic uses.

In various embodiments, the modified hsps or modified hsp-antigenic peptide complexes can be purified by affinity chromatography and used as a vaccine for the prevention and treatment of cancer or infectious diseases.

The immunogenic compositions, including modified hsp-peptide complexes as well as recombinant cells secreting modified hsp-peptide complexes, prepared according to the methods of the invention can induce an immune response in a patient against the cancer cells or the infectious agent that is therapeutically or prophylactically efficacious. Preferably, the patient is the subject who provided the cancer cells for expression of a modified hsp. Alternatively, the cancer cells or infected cells can be from one or more subjects different from the patient but having cancer of the same tissue type (e.g., stomach cancer, breast cancer, colon cancer, lung cancer, etc), or infectious diseases caused by the same type of pathogen.

Accordingly, the invention provides methods of eliciting an immune response against an antigen in an individual comprising administering to the individual an immunogenic complex of a modified heat shock protein non-covalently associated with the antigen or a fragment thereof, and/or a recombinant cell secreting such an immunogenic complex. The invention also provides methods of treating or preventing cancer in an individual having cancer or in whom prevention of cancer is desired comprising administering to the individual an immunogenic complex of a modified heat shock protein non-covalently associated with an antigen or a fragment thereof derived from the cancer, and/or a recombinant cell that is secreting such an immunogenic complex. Further, the invention provides methods of treating or preventing an infectious disease in an individual having an infectious disease or in whom prevention of an infectious disease is desired comprising administering to the individual an immunogenic complex of a modified heat shock protein non-covalently associated with an antigen or a fragment thereof derived from an infected cell or an infectious agent, and/or a recombinant cell that is secreting such an immunogenic complex.

Particular compositions of the invention and their methods of preparation are described in the sections and subsections which follow.

4. BRIEF DESCRIPTION OF THE DRAWING

FIGS. 1a-1c. Gp96-Ig secretion and characterization, FIG. 1a: ELISA for murine IgG of supernatants from gp96-Ig cDNA transfected and untransfected small cell lung carcinoma line #7 (SCLC); cells were plated at $10^6$/ml and supernatants tested on day 3 and day 6; purified mouse IgG (500 ng/ml) served as standard. FIG. 1b: SDS PAGE of protein A purified gp96-Ig. lane 1: Coomassie blue stain (1 µg protein), lane 2: Western blot with monoclonal anti gp96 (anti Grp94, 9G10) (100 ng protein). FIG. 1C: Sodium dodecyl sulfate-polyacrylamide gel electrophoresis (SDS-PAGE) analysis of purified modified gp96-Ig fusion protein (gp96-Ig), in comparison to mouse IgG (mIgG), and CD30-Ig fusion protein (CD30-Ig) under reducing and non-reducing conditions. Molecular weight markers (in kDa) are indicated on the left.

FIGS. 2a-2d: Secretion and intracellular localization of gp96-Ig. FIG. 2a: Solid circles: gp96-Ig in the culture supernatant, open circles: gp96-Ig in cell lysates. GP96-Ig was quantitated by ELISA; SCLC-gp96-Ig were plated at $10^6$/ml FIG. 2b: FACS analysis of permeabilized SCLC-gp96-Ig; dashed line, goat anti rabbit IgG-FITC (negative control); solid line, goat anti mouse IgG-phycoerythrin. FIG. 2c: FACS analysis of unpermeabilized SCLC; untransfected. FIG. 2d: FACS analysis of unpermeabilized SCLC; gp96-Ig transfected SCLC. Dashed line in both panels is goat anti rabbit IgG-FITC; solid line, goat anti mouse IgG-FITC.

FIGS. 3a-3b: Decreased tumorigenicity of gp96-Ig transfected E.G7 (FIG. 3a) and LLC (FIG. 3b) (solid circles), in comparison to mock transfected (triangles) and untransfected cells (open circles). Groups of six mice were used per parameter FIGS. 4a-4d: Secretory gp96-Ig generates tumor specific memory. C57BL/6 mice were immunized twice in biweekly intervals with $10^6$ gp96-Ig transfected E.G7 (solid circles in all panels), with $10^6$ irradiated EG7 (triangles) or not immunized (open circles). Two weeks later mice were challenged (six mice per group) with the number of tumor cells as indicated in the Figures: FIG. 4a: E.G7; FIG. 4b: EL4; FIG. 4c: LLC; FIG. 4d: LLC-ova.

FIGS. 5a-5h: Effect of depletion of immuno-competent cells on rejection of $10^6$ E.G7-gp96-Ig. Tumor growth curves in individual mice are shown. FIGS. 5a-5d (upper panels): Depletion of immuno-competent cells two days prior to subcutaneous tumor inoculation. FIGS. 5e-5h (lower panels): Depletion of immuno-competent cells three days after subcutaneous tumor inoculation.

5. DETAILED DESCRIPTION OF THE INVENTION

The present invention contemplates the application of recombinant DNA technology to modify heat shock proteins which are involved in antigen presentation, and to prepare immunogenic compositions that can be used for the prevention and treatment of cancer and infectious diseases.

The "antigenic cells" used in the invention can be any antigenic cells, including but not limited to cancer cells, preneoplastic cells, cells infected with an intracellular pathogen, or cells obtained from a subject infected with an infectious agent.

Immunogenic hsp-peptide complexes are produced naturally in cancer cells or pathogen-infected cells. Such hsp-peptide complexes have been used to elicit in a recipient of the complexes a specific immune response against the same kind of cancer cells or infected cells, and thus, are useful for the prevention and treatment of the cancer or infectious diseases. However, such immunogenic complexes are generally not secreted by these cells in large amounts. Furthermore, as it is not always possible or feasible to obtain large number of cancer cells or infected cells (antigenic cells), the quantity of the hsp-peptide complexes obtainable from such cells is sometimes very limited. It is therefore desirable to find ways to overcome the problem of having a limited supply of the immunogenic hsp-peptide complexes. Part of the problem is due to the methods of purifying hsp-peptide complexes as currently practiced which require lysis of the cells. The present invention provides methods for causing immunogenic hsp-peptide complexes to be secreted by antigenic cells into the culture medium. The antigenic cells of the invention can continuously produce and secrete the desired immunogenic complexes which are conveniently harvested from the culture medium. Improved methods for purifying such immunogenic complexes from the culture medium are also provided. Moreover, the invention provides methods for enhancing the immunogenicity of cancer cells and infected cells, such that these antigenic cells can be administered directly to a subject as a vaccine to prevent and treat cancer or infectious diseases.

In one embodiment, the immunogenic compositions prepared by the methods of the invention comprise noncovalently associated molecular complexes containing a modified heat shock protein (hsp) and an antigenic peptide that is present or that is a portion of a protein that is present in an antigenic cell. The modified heat shock protein of the invention is secreted by a cell in which it is expressed; lacks an endoplasmic reticulum retention sequence present in the unmodified heat shock protein; and comprises a peptide tag. When the modified hsps are expressed in recombinant cells, they are secreted and can be purified by the peptide tag using affinity chromatography.

In another embodiment, a modified heat shock protein of the invention is secreted by a cell in which it is expressed; comprises a peptide tag; and comprises a leader peptide not present in the unmodified heat shock protein. For those hsps that naturally reside in the cytoplasm, the leader peptide added to the amino terminus facilitate their translocation into the ER.

The modified hsps of the invention exhibit the same qualitative biological activity as the naturally occurring hsps. The modifications does not affect the abilities of the modified hsp to bind specifically and non-covalently antigenic peptides, and to present such bound peptides to the relevant immune cells in the course of antigen presentation. Thus, the modified hsps can form immunogenic non-covalent complexes with antigenic peptides both in vitro and in antigenic cells. Modified hsp-peptide complexes formed endogenously in antigenic cells and in vitro are both capable of inducing a specific immune response in a animal against the antigenic cells from which the antigenic peptides are derived.

In particular, the invention relates to the modification of nucleotide sequences encoding heat shock protein (hsp) that are naturally retained in the endoplasmic reticulum of an animal cell. According to the invention, a hsp gene sequence, preferably a cDNA sequence, is modified by substitution or deletion of portions of the hsp sequence that encode a stretch of peptide that signals retention of the hsp in the ER. The signal for retention of a hsp in the ER is known to reside in a stretch of located at the carboxyl terminal. The hsp gene sequence is further modified by adding a nucleotide sequence encoding a peptide tag to the hsp sequence. The resulting modified hsp sequence of the invention encodes a modified hsp fusion protein that is secreted and not retained in the ER.

For a hsp that naturally resides in the cytoplasm, its gene sequence is modified by, adding not only a nucleotide sequence encoding a peptide tag, but also a nucleotide sequence encoding a leader peptide. This sequence is joined to the 5' end of the coding region of the hsp gene sequence. Hsps carrying such a hydrophobic leader peptide are imported into the ER lumen. The leader peptide is recognized by a signal recognition particle which directs the growing hsp peptide chain to the cytosolic surface of rough ER membranes. Secretable hsps is translocated across the membrane completely into the lumen where the leader peptide is digested by proteases.

A variety of peptide tags with different functions and affinities can be used in the invention to facilitate the purification of the modified hsp or modified hsp-peptide complexes by affinity chromatography. A preferred peptide tag comprises the constant regions of an immunoglobulin. Depending on the peptide tag fused to a hsp, the modified hsp may acquire novel properties, such as dimerization, that may be advantageously exploited to enhance the function of the modified hsp or modified hsp-peptide complexes. Sequences encoding peptide tags and leader peptides, and methods for joining such sequences to hsp sequences are described in Section 5.1.4.

Accordingly, the invention provides nucleic acid molecules comprising nucleotide sequences encoding modified hsps ("modified hsp gene sequences"), and cloning vectors, expression vectors, and recombinant cells containing such sequences. The invention also encompasses nucleic acid molecules comprising nucleotide sequences that are complementary to the modified hsp gene sequences. A modified hsp gene sequence can be cloned and/or expanded by replication in a cloning vector in an intermediate cell, prior to introduction into suitable host cells for production of modified hsp-peptide complexes. Expression constructs or expression vectors comprising a modified hsp gene sequence can be constructed and introduced into the host cells by any methods known in the art as described in Section 5.2.1. Depending on needs, a variety of cells can be used for expression of the modified hsp, including cancer cells, pathogen-infected cells, or normal cells.

The expression gene construct of the invention comprises a nucleotide sequence encoding a modified hsp, preferably a complementary DNA (cDNA) sequence encoding a modified hsp. The modified hsp gene sequence is operably associated with at least one regulatory region (e.g., promoter) that controls expression of the modified hsp sequence in an appropriate host cell. Alternatively, the modified hsp sequence may be flanked by regions promoting homologous recombination within the host cell so as to insert the modified hsp sequence in an intrachromosomal position so that the modified hsp sequence is operably associated with at least one regulatory region that controls expression of the modified hsp sequence in the host cell. Both types of expression gene constructs comprising a modified hsp gene sequence are also referred to as an expressible modified hsp gene sequence. Accordingly, the invention provides a recombinant cell containing an expressible modified hsp gene sequence.

Sequences encoding hsps and sequences encoding peptide tags, and methods for obtaining such sequences are described in details in Section 5.1.1 and 5.1.4. Methods for modifying the hsp gene sequence by adding, deleting or substituting nucleotides are described in Section 5.1.2.

In another embodiment, the invention provides methods for purifying modified hsps from cell cultures comprising culturing the recombinant cells to allow expression of the modified hsp gene sequence, and recovering and purifying the modified hsp that is secreted from the recombinant cells. Generally, purification of the secreted modified hsps from the culture supernatant is facilitated by the peptide tag on the modified hsp using the appropriate affinity chromatographic method, such as those described in Section 5.3. The improved methods do not require lysing the cells which is allowed to grow continuously and produce modified hsps or modified hsp-peptide complexes.

Since the modified hsps of the invention are capable of binding peptides like the unmodified hsps, upon expression of the modified hsp gene sequence in a recombinant antigenic cell, the modified hsp is produced which become associated with peptides in the ER to form noncovalent complexes. Because some of the proteins of the antigenic cells are antigenic/immunogenic, peptides/proteins that complex with the modified hsps confer specific immunity to a host against the antigenic cell in which they are present. Such non-covalent immunogenic complexes are secreted by the recombinant cells and accumulate in the culture medium.

Accordingly, the invention also provides methods for producing as well as purifying immunogenic non-covalent complexes of modified hsps and antigenic peptides in cells. In one embodiment, the method comprises introducing a modified hsp gene sequence into antigenic cells, culturing the recombinant antigenic cells to allow expression of the modified hsp gene sequence, and recovering and purifying from the culture medium the modified hsp-antigenic peptide complexes that is secreted from the recombinant antigenic cells. The antigenic peptides of the complexes are representative of antigenic peptides found inside the antigenic cells, and there is no need to isolate and/or characterize the antigens, or even know the identities of these antigens, prior to using the antigenic peptide to vaccinate a subject. Methods applicable to the purification of modified hsps from cell culture medium, such as those described in Section 5.3, are also useful in purifying modified hsp-antigenic peptide complexes, provided that the methods do not disrupt the non-covalent associations of the modified hsps and antigenic peptides. In a specific embodiment, the recombinant antigenic cells comprising an expressible modified hsp gene sequences can be used in an immunogenic composition for therapeutic and prophylactic uses. The immunogenicity of such compositions can be tested by methods known in the art and described in Section 5.5, and Section 6. For purpose of preparing modified hsp which is to be used for making hsp-peptide complexes in vitro, it may be desirable to use host cells that are not itself antigenic so that the secreted modified hsp does not become loaded with unwanted antigenic molecules.

By culturing the recombinant cells continuously or in batch, in a suitably large scale, modified hsp or modified hsp-peptide complexes can be produced in large amounts. A desirable immunogenic complex comprising a modified hsp and recombinantly produced antigenic proteins/peptides can be purified from the cell culture medium of large-scale continuous or batch culture of the recombinant antigenic cells. A permanent cell line secreting modified hsp-peptide complexes can provide a consistent, reproducible and abundant source of the useful immunogenic composition. Depending on needs, recombinant cells containing a modified hsp gene sequence can be pooled and/or aliquoted; or expanded; or archived by freezing down and storing under liquid nitrogen, so that batches of the recombinant host cells can be retrieved and used many times in the future.

In another embodiment where the coding sequence of an antigenic protein or peptide is known, it is contemplated that such sequence encoding the antigenic molecule can be cloned into an expression gene construct, and introduced into a recombinant cell containing an expressible modified hsp sequence. The cloning of an antigenic protein or peptide into an expression vector can be carried out by standard techniques, such as those described for the expression of the modified hsp (see Section 5.2). The antigenic protein or peptide is co-expressed with a modified hsp in the recombinant cell. These antigenic proteins or peptides form non-covalent complexes with the modified hsp in the ER of the recombinant cell. Such antigenic peptide can be a fragment of an antigenic protein expressed in the cancer cell, such as for example, fragment of a tumor-specific antigen or tumor associated antigen. The modified hsp-antigenic peptide complexes from these cells are secreted into the culture medium, and can likewise be recovered and purified by affinity chromatography as described in Section 5.3. The recombinant cells containing both an expressible modified hsp sequence as well as the expression gene construct encoding the antigen can also be used as an immunogenic composition for therapeutic and prophylactic uses.

The invention further provides that purified modified hsps can be loaded with antigenic peptides to form immunogenic non-covalent complexes in vitro. Such complexes are useful in the treatment and prevention of cancer or infectious diseases. Antigenic peptides can be purified from cellular sources, or they can be synthesized, if the sequences of the peptides are known, by methods known in the art. In a specific embodiment, antigenic peptides are incubated with modified hsps which have been reversibly immobilized onto a solid phase by its peptide tag, such that non-covalent complexes of antigenic peptides and modified hsps are formed on the solid phase.

Accordingly, the invention provides a method for preparing complexes of a modified heat shock protein of the invention noncovalently associated with a peptide in vitro comprising incubating modified heat shock proteins and peptides for a time sufficient for the formation of the complexes.

The immunogenic compositions of the invention including both modified hsp-peptide complexes and recombinant antigenic cells prepared by the claimed methods can enhance the immunocompetence of an individual and elicit specific immunity against both neoplastic cells, as well as pathogen-infected cells. Such immunogenic compositions are also capable of preventing the development of tumors and inhibiting the growth and progression of tumor cells, and preventing the growth of pathogens or cells infected with pathogens. The immunogenic compositions can be used to induce an inflammatory reaction at the tumor site and ultimately cause a regression of the tumor burden in the cancer patients treated.

Accordingly, the invention provides a method of eliciting an immune response against an antigen in an individual comprising administering to the individual an immunogenic complex of a modified heat shock protein of the invention non-covalently associated with the antigen or a fragment thereof. The invention also provides a method of treating or preventing cancer in an individual having cancer or in whom prevention of cancer is desired comprising administering to the individual an immunogenic complex of a modified heat shock protein of the invention non-covalently associated with the antigen or a fragment thereof. Also encompassed in the invention is a method of treating or preventing an infectious disease in an individual having an infectious disease or in whom prevention of an infectious disease is desired comprising administering to the individual an immunogenic complex of a modified heat shock protein of the invention non-covalently associated with the antigen or a fragment thereof.

The immunogenic compositions can be administered autologously to the individual from whom the cancer cells or tissues were obtained, or to individuals at enhanced risk of cancer due to familial history or environmental risk factors. Likewise, the immunogenic compositions can be administered autologously to the individual from whom the pathogen-infected cells or antigenic cells were obtained, or to individuals at risk of being infected by the same pathogen.

The methods of treatment or prevention of cancer are also generally applicable to other individuals that did not provide the cancer cells for expression of the modified hsp, so long as they have the same type of cancer as the provider of the cancer cells. The same principle applies to the treatment or prevention of infectious diseases in that the method is applicable to other individuals so long as they are infected with infectious agents that are antigenically similar to the infectious agent that infected the provider of the antigenic host cells. The uses of the immunogenic compositions to treat or prevent cancer and infections diseases are described in Sections 5.7 and 5.8.

5.1. Construction of Modified HSP Gene Sequences

Described herein are methods for the construction of a gene construct encoding a modified heat shock protein (hsp) that can be expressed in prokaryotic and eukaryotic cells. Specifically described are the construction of a nucleotide sequence encoding a modified hsp, the insertion of the modified hsp gene sequence into an appropriate cloning vector, and the introduction of the expression gene construct into the appropriate host cell for production of modified hsp and modified hsp-peptide complexes.

Heat shock proteins, which are referred to interchangeably herein as stress proteins, useful in the treatment and prevention of cancer or infectious diseases, can be selected from among any cellular protein that satisfies any one of the following criteria. It is a protein whose intracellular concentration increases when a cell is exposed to a stressful stimuli, it is capable of binding other proteins or peptides, and it is capable of releasing the bound proteins or peptides in the presence of adenosine triphosphate (ATP) or low pH; or it is a protein showing at least 35% homology with any cellular protein having any of the above properties. The hsps in the complexes that can be modified and prepared by the present invention include but are not limited to, hsp70, hsp90, gp96, BiP, and protein disulfide isomerase. Preferably, the hsps are human hsps. Preferred complexes comprise modified human hsp60, hsp70, hsp90, protein disulfide isomerase, or BiP noncovalently bound to a protein antigen. In a specific embodiment, the complex comprises a modified form of human gp96 which is normally resident in the endoplasmic reticulum of eukaryotic cells.

Three major families of hsp, namely hsp60, hsp70 and hsp90, have been identified so far. In addition, protein disulfide isomerase (PDI), and other proteins in the endoplasmic reticulum that contain thioredoxin-like domain(s), such as but not limited to ERp72 and ERp61, are also encompassed. It is contemplated that members of all of these hsp families can be modified and prepared by the practice of the instant invention.

It has been discovered that the hsp60, hsp70, hsp90 and protein disulfide isomerase families are composed of proteins that are related to the stress proteins in sequence, for example, having greater than 35% amino acid identity, but whose expression levels are not altered by stress. Therefore it is contemplated that the definition of stress or heat shock protein, as used herein, embraces other proteins, muteins, analogs, and variants thereof having at least 35% to 55%, preferably 55% to 75%, and most preferably 75% to 85% amino acid identity with members of these families whose expression levels in a cell are enhanced in response to a stressful stimulus.

The procedures described in standard treatises, e.g., Methods in Enzymology, 1987, volume 154, Academic Press; Sambrook et al., 1989, Molecular Cloning—A Laboratory Manual, 2nd Edition, Cold Spring Harbor Press, New York; and Ausubel et al., Current Protocols in Molecular Biology, Greene Publishing Associates and Wiley Interscience, New York, may be followed to carry out routine molecular biology reactions used in constructing and modifying the hsp gene construct. Methods described in detail infra are for illustration only and not by way of limitation. Various cloning vectors and expression systems that are commercially available may also be used according to the manufacturer's instructions.

5.1.1. Isolation of Hsp Gene Sequences

In various aspects, the invention relates to amino acid sequences of modified heat shock proteins (hsps), and fragments and derivatives thereof, which are functionally active. "Functionally active" modified hsp as used herein refers to modified hsps which display one or more known functional activities associated with the unmodified hsp, such as the binding of antigenic peptide, the release of bound antigenic peptide in the presence of adenosine triphosphate (ATP), or low pH, etc. Nucleic acids encoding the modified hsps and fragments thereof described above are provided, as well as nucleic acids complementary to and capable of hybridizing to such nucleic acids.

Amino acid sequences and nucleotide sequences of naturally occurring heat shock proteins are generally available in sequence databases, such as GenBank. Computer programs, such as Entrez, can be used to browse the database, and retrieve any amino acid sequence and genetic sequence data of interest by accession number. These databases can also be searched to identify sequences with various degrees of similarities to a query sequence using programs, such as FASTA and BLAST, which rank the similar sequences by alignment scores and statistics.

The nucleotide sequences of non-limiting examples of hsps that can be modified and expressed by methods of the invention are published as follows: human gp96: Genebank Accession No. X15187; Maki et al., 1990, Proc. Natl. Acad. Sci., 87: 5658-5562. mouse gp96: Genebank Accession No. M16370; Srivastava et al., 1987, Proc. Natl. Acad. Sci., 85:3807-3811; mouse BiP: Genebank Accession No. U16277; Haas et al., 1988, Proc. Natl. Acad. Sci. U.S.A., 85: 2250-2254, human BiP: Genebank Accession No. M19645; Ting et al., 1988, DNA 7: 275-286; mouse hsp70: Genebank Accession No. M35021, Hunt et al., 1990, Gene, 87:199-204, human hsp70, Genbank Accession No. M24743; Hunt et al., 1995, Proc. Natl. Acad. Sci. U.S.A., 82: 6455-6489. Due to the degeneracy of the genetic code, the term "hsp gene sequence" refers not only to the naturally occurring nucleotide sequence but also encompasses all the other degenerate DNA sequences that encode the hsp.

Any eukaryotic cell potentially can serve as the nucleic acid source for obtaining the coding region of a hsp gene. Nucleic acid sequences encoding hsps can be isolated from vertebrate, mammalian, as well as primate sources, including humans.

The DNA may be obtained by standard procedures known in the art from cloned DNA (e.g., a DNA "library"), or by DNA amplification. Clones derived from genomic DNA may contain regulatory and intron DNA regions in addition to coding regions; clones derived from cDNA will contain only exon sequences. Whatever the source, the hsp gene should be molecularly cloned into a suitable vector for propagation of the gene.

In the molecular cloning of a hsp gene from genomic DNA, DNA fragments are generated and cloned to form a genomic library. Since some of the sequences encoding related hsps are available and can be purified and labeled, the cloned DNA fragments in the genomic DNA library may be screened by nucleic acid hybridization to the labeled probe (Benton, W. and Davis, R., 1977, Science 196:180; Grunstein, M. And Hogness, D., 1975, Proc. Natl. Acad. Sci. U.S.A. 72:3961). Those DNA fragments with substantial homology to the probe will hybridize. It is also possible to identify the appropriate fragment by restriction enzyme digestion(s) and comparison of fragment sizes with those expected according to a known restriction map if such is available.

Alternatives to isolating the hsp genomic DNA include, but are not limited to, chemically synthesizing the gene sequence itself from a known sequence or making cDNA to the mRNA which encodes the hsp. For example, RNA for cDNA cloning of the hsp gene can be isolated from cells which express the hsp. A cDNA library may be generated by methods known in the art and screened by methods, such as those disclosed for screening a genomic DNA library. If an antibody to the hsp is available, the hsp may be identified by binding of labeled antibody to the putatively hsp synthesizing clones.

Other specific embodiments for the cloning of a nucleotide sequence encoding a hsp, are presented as examples but not by way of limitation, as follows:

In a specific embodiment, nucleotide sequences encoding heat shock protein within a family can be identified and obtained by hybridization with a probe comprising nucleotide sequence encoding a hsp under conditions of low to medium stringency.

By way of example and not limitation, procedures using such conditions of low stringency are as follows (see also Shilo and Weinberg, 1981, Proc. Natl. Acad. Sci. USA 78:6789-6792). Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10$^6$ cpm $^{32}$P-labeled probe is used. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65-68° C. and reexposed to film. Other conditions of low stringency which may be used are well known in the art (e.g., as employed for cross-species hybridizations).

In another embodiment, polymerase chain reaction (PCR) is used to amplify the desired sequence in DNA clone or a genomic or cDNA library, prior to selection. PCR can be carried out, e.g., by use of a thermal cycler and Taq polymerase (GeneAmp™). The DNA being amplified can include cDNA or genomic DNA from any species. Oligonucleotide primers representing known nucleic acid sequences of related hsps can be used as primers in PCR. In a preferred aspect, the oligonucleotide primers represent at least part of the hsp gene that is highly conserved between hsps of different species. One can choose to synthesize several different degenerate primers, for use in the PCR reactions. It is also possible to vary the stringency of hybridization conditions used in priming the PCR reactions, to allow for greater or lesser degrees of nucleotide sequence similarity between the known hsp nucleotide sequence and the nucleic acid homolog being isolated. For cross species hybridization, low stringency conditions are preferred. For same species hybridization, moderately stringent conditions are preferred. After successful amplification, the sequence encoding a hsp may be cloned and sequenced. If the size of the coding region of the hsp gene being amplified is too large to be amplified in a single PCR, several PCR covering the entire gene, preferably with overlapping regions, may be carried out, and the products of the PCR ligated together to form the entire coding sequence. Alternatively, if a segment of a hsp gene is amplified, that segment may be cloned, and utilized as a probe to isolate a complete cDNA or genomic clone.

Prior to modification, the hsp gene can be inserted into an appropriate cloning vector and introduced into host cells so that many copies of the gene sequence are generated. A large number of vector-host systems known in the art may be used such as, but not limited to, bacteriophages such as lambda derivatives, or plasmids such as pBR322 or pUC plasmid derivatives or the Bluescript vector (Stratagene).

The above methods are not meant to limit the methods by which clones of hsps may be obtained or propagated. The modified heat shock proteins of the invention are modified such that they are secreted and can be easily purified from the cell culture medium. In particular, a modified hsp of the invention lacks a segment of the polypeptide that signals retention of the hsp in the endoplasmic reticulum (ER). The retention signal is disabled by deleting the peptide, or by substitution with a peptide that does not function as a signal. In addition, the modified hsp comprises a peptide tag which facilitates recovery and purification. The peptide tag can be fused to any portion of the hsp that is not involved in binding antigenic peptide, such as for example, the carboxyl terminal. Further, if the hsp resides naturally in the endoplasmic reticulum, a leader peptide is added to direct its translocation across the ER membrane for secretion. In a preferred embodiment, the retention peptide of a hsp which is usually located at the carboxyl terminus is replaced by a peptide tag.

5.1.2 Modification of Heat Shock Protein Genes

The modified heat shock proteins of the invention are modified such that they are secreted by the cells in which they are expressed, and can be easily purified from the cell culture medium. In particular, a modified hsp of the invention lacks a segment of the polypeptide that signals retention of the hsp in the endoplasmic reticulum (ER). Such a peptide is found in hsps that remain in the ER, such as but not limited to gp96. The retention signal is disabled by deleting the peptide, or by substitution with a peptide that does not function as a signal. In addition, the modified hsp comprises a peptide tag which facilitates recovery and purification. The peptide tag can be fused to any portion of the hsp that is not involved in binding antigenic peptide, such as for example, the carboxyl terminal. In a preferred embodiment, the retention peptide of a hsp which is usually located at the carboxyl terminus is replaced by a peptide tag. Further, if the hsp resides naturally in the cytoplasm, a leader peptide is added to direct its translocation across the ER membrane for secretion.

The modifications present in modified hsps of the invention can be produced by various methods known in the art. The manipulations which result in their production can occur at the gene or protein level, preferably at the gene level. For example, the cloned coding region of a hsp can be modified by any of numerous recombinant DNA methods known in the art (Sambrook et al., 1990, Molecular Cloning, A Laboratory Manual, 2d ed., Cold Spring Harbor Laboratory, Cold Spring Harbor, N.Y.; Ausubel et al., in Chapter 8 of Current Protocols in Molecular Biology, Greene Publishing Associates and Wiley Interscience, New York). It will be apparent from the following discussion that substitutions, deletions, insertions, or any combination thereof are introduced or combined to arrive at a final nucleotide sequence encoding a modified hsp.

Alternatively, modified hsp can be chemically synthesized. For example, a peptide corresponding to a portion of a hsp which comprises the desired modifications can be synthesized by use of a peptide synthesizer.

5.1.3 Retention Peptide

The peptide that causes a hsp to remain in the endoplasmic reticulum (ER) is located typically at the carboxyl terminal (Munro & Pelham, 1987, Cell, 48:899-907). The term "retention peptide" is used herein to refer to this tetrapeptide sequence.

The retention peptide of hsps can be disabled either by deleting the retention peptide, or by obliterating the signal with amino acid substitutions in the retention peptide. As a general proposition, any signals present in the modified hsp sequence that, if present, tend to prevent the modified hsp from secretion by the cell should be removed. Depending on the individual hsp, such signals may include transmembrane domains, and cytoplasmic domains.

In order to remove the segment of DNA encoding the retention peptide sequence or other signals, the hsp gene sequence can be cleaved at appropriate sites with restriction endonuclease(s) if such sites are available, releasing a fragment of DNA encoding the retention peptide. The remainder of the hsp coding region is then isolated, and ligated to form the modified hsp gene sequence.

Alternatively, if convenient restriction sites are not available, a larger fragment of DNA can be released by using restriction sites located in sequences flanking the region that encodes the retention peptide sequence, and replaced by a similar fragment of synthetic DNA which lacks the sequence encoding the retention peptide. Care must be taken to ensure that the proper translation reading frame is maintained.

If it is desirable, restriction sites can be created in the appropriate positions by site-directed mutagenesis methods and/or DNA amplification methods known in the art. See, for example, Shankarappa et al., 1992, PCR Method Appl. 1:277-278. The polymerase chain reaction (PCR) is commonly used for introducing desired sequence changes into the DNA of interest. Any changes in primer sequence can be easily incorporated into the DNA product of PCR which facilitates subsequent incorporation of the changes into the gene sequence. For example, synthetic oligonucleotides incorporating the desired restriction site are used in conjunction with the appropriate flanking sequence primers to amplify two adjacent fragments of DNA. Each of these amplified fragments will contain the new restriction site at one end. Following enzymatic digestion at both the new and flanking sites, the amplified fragments are ligated and subcloned into a vector ready for further manipulations. It is imperative that the introduction of restriction sites does not alter the amino acid sequence of the encoded protein.

Any technique for mutagenesis known in the art can be used to modify individual nucleotides in a DNA sequence, for purpose of making amino acid substitution(s) in the expressed peptide sequence, or for creating/deleting restriction sites to facilitate further manipulations. Such techniques include but are not limited to, chemical mutagenesis, in vitro site-directed mutagenesis (Hutchinson, C., et al., 1978, J. Biol. Chem 253:6551), oligonucleotide-directed mutagenesis (Smith, 1985, Ann. Rev. Genet. 19:423-463; Hill et al., 1987, Methods Enzymol. 155:558-568), PCR-based overlap extension (Ho et al., 1989, Gene 77:51-59), PCR-based megaprimer mutagenesis (Sarkar et al., 1990, Biotechniques, 8:404-407), etc. Modifications can be confirmed by double stranded dideoxy DNA sequencing.

The above method can be applied to substitute one or more of the amino acid residues in the tetrapeptide retention sequence especially the Asp, Glu, and Leu residues. Substitutes for an amino acid within the retention peptide sequence may be selected from members of a different class to which the amino acid belongs. The nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. The substitution which in general are expected to produce the greatest changes in biochemical properties will be those in which (a) a hydrophilic residue, e.g., seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g, phenylalanine, is substituted for (or by) one not having a side chain, e.g., glycine.

The above methods are not meant to limit the methods by which the retention peptide sequence and/or other signal can be deleted or obliterated in a hsp.

5.1.4 Peptide Tag and/or Leader Peptide Fusion

The modified hsp of the invention is also a fusion protein comprising a peptide tag. In certain embodiments, a leader peptide may also be fused to a modified hsp thereby facilitating the transport of the modified hsp into the endoplasmic reticulum (ER) for secretion.

In various embodiments, such a fusion protein can be made by ligating a hsp gene sequence to the sequence encoding the peptide tag or the leader peptide in the proper reading frame. If genomic sequences are used, care should be taken to ensure that the modified gene remains within the same translational reading frame, uninterrupted by translational stop signals and/or spurious messenger RNA splicing signals.

In a preferred embodiment, the peptide tag is fused at its amino terminal to the carboxyl terminal of the hsp. The precise site at which the fusion is made in the carboxyl terminal is not critical. For example, the peptide tag may take the place of the retention peptide. The optimal site can be determined by routine experimentation. The immunogenicities of the modified hsp can be tested by methods described in Section 5.5.

A variety of peptide tag known in the art may be used in the modification of a hsp, such as but not limited to the immunoglobulin constant regions, polyhistidine sequence (Petty, 1996, Metal-chelate affinity chromatography, in Current Protocols in Molecular Biology, Vol. 2, Ed. Ausubel et al., Greene Publish. Assoc. & Wiley Interscience), glutathione S-transferase (GST; Smith, 1993, Methods Mol. Cell Bio. 4:220-229), the *E. coli* maltose binding protein (Guan et al., 1987, Gene 67:21-30), and various cellulose binding domains (U.S. Pat. Nos. 5,496,934; 5,202,247; 5,137,819; Tomme et al., 1994, Protein Eng. 7:117-123), etc. Some peptide tags may afford the modified hsp novel structural properties, such as the ability to form multimers. Dimerization of modified hsp with a bound peptide may increase avidity of interaction between the hsp and its partner in the course of antigen presentation. These peptide tags are usually derived from proteins that normally exist as homopolymers. Peptide tags such as the extracellular domains of CD8 (Shiue et al., 1988, J. Exp. Med. 168:1993-2005), or CD28 (Lee et al., 1990, J. Immunol. 145:344-352), or portions of the immunoglobulin molecule containing sites for interchain disulfide bonds, could lead to the formation of multimers. Other possible peptide tags are short amino acid sequences to which monoclonal antibodies are available, such as but not limited to the following well known examples, the FLAG epitope, the myc epitope at amino acids 408-439, the influenza virus hemaglutinin (HA) epitope. Other peptide tags are recognized by specific binding partners and thus facilitate isolation by affinity binding to the binding partner, which is preferably immobilized and/or on a solid support. As will be appreciated by those skilled in the art, many methods can be used to obtain the coding region of the above-mentioned peptide tags, including but not limited to, DNA cloning, DNA amplification, and synthetic methods. Some of the peptide tags and reagents for their detection and isolation are available commercially.

A preferred peptide tag is a non-variable portion of the immunoglobulin molecule. Typically, such portions comprises at least a functionally CH2 and CH3 domains of the constant region of an immunoglobulin heavy chain. Fusions are also made using the carboxyl terminus of the Fc portion of a constant domain, or a region immediately amino-terminal to the CH1 of the heavy or light chain. Suitable immunoglobulin-based peptide tag may be obtained from IgG-1, -2, -3, or -4 subtypes, IgA, IgE, IgD, or IgM, but preferably IgG1. Preferably, a human immunoglobulin is used when the modified hsp is intended for in vivo use for humans. Many DNA encoding immunoglobulin light or heavy chain constant regions is known or readily available from cDNA libraries. See, for example, Adams et al., Biochemistry, 1980, 19:2711-2719; Gough et al., 1980, Biochemistry, 19:2702-2710; Dolby et al., 1980, Proc. Natl. Acad. Sci. U.S.A., 77:6027-6031; Rice et al., 1982, Proc. Natl. Acad. Sci. U.S.A., 79:7862-7865; Falkner et al., 1982, Nature, 298:286-288; and Morrison et al., 1984, Ann. Rev. Immunol, 2:239-256.

Because many immunological reagents and labeling systems are available for the detection of immunoglobulins, the modified hsp-Ig fusion protein ("modified hsp-Ig") can readily be detected and quantified by a variety of immunological techniques known in the art, such as the use of enzyme-linked immunosorbent assay (ELISA), immunoprecipitation, fluorescence activated cell sorting (FACS), etc. Similarly, if the peptide tag is an epitope with readily available antibodies, such reagents can be used with the techniques mentioned above to detect, quantitate, and isolate modified hsp containing the peptide tag. In many instances, there is no need to develop specific antibodies to the modified hsp.

A particularly preferred embodiment is a fusion of a modified hsp, which lacks the retention peptide, to the hinge, CH2 and CH3 domains of murine immunoglobulin G-1 (IgG-1) (Bowen et al., J. Immunol. 156:442-9). This peptide contains three cysteine residues which are normally involved in disulfide bonding with other cysteines in the Ig molecule. Since none of the cysteines are required for the peptide to function as a tag, one or more of these cysteine residues may optionally be substituted by another amino acid residue, such as for example, serine. Methods such as those described in Section 5.1.2 can be applied to make such substitutions.

Various leader sequences known in the art can be used for the efficient secretion of modified hsps from bacterial and mammalian cells (von Heijne, 1985, J. Mol. Biol. 184:99-105). Leader peptides are selected based on the intended host cell, and may include bacterial, yeast, viral, animal, and mammalian sequences. For example, the herpes virus glycoprotein D leader peptide is suitable for use in a variety of mammalian cells. A preferred leader peptide for use in mammalian cells can be obtained from the V-J2-C region of the mouse immunoglobulin kappa chain (Bernard et al., 1981, Proc. Natl. Acad. Sci. 78:5812-5816).

DNA sequences encoding desired peptide tag or leader peptide which are known or readily available from libraries or commercial suppliers are suitable in the practice of this invention. Methods for obtaining hsp sequences described in Section 5.1.1 can also be applied to obtain sequences encoding a peptide tag or leader peptide.

5.2 Production of Modified Hsps

In various embodiments of the invention, sequences encoding modified hsps are inserted into an expression vector for propagation and expression in recombinant cells.

An expression construct, as used herein, refers to a nucleotide sequence encoding a modified hsp operably associated with one or more regulatory regions which enables expression of the modified hsp in an appropriate host cell. "Operably-associated" refers to an association in which the regulatory regions and the modified hsp sequence to be expressed are joined and positioned in such a way as to permit transcription, and ultimately, translation.

The regulatory regions necessary for transcription of the modified hsp can be provided by the expression vector. A translation initiation codon (ATG) may also be provided if the modified hsp sequence lacking its cognate initiation codon is to be expressed. In a compatible host-construct system, cellular transcriptional factors, such as RNA polymerase, will bind to the regulatory regions on the expression construct to effect transcription of the modified hsp sequence in the host organism. The precise nature of the regulatory regions needed for gene expression may vary from host cell to host cell. Generally, a promoter is required which is capable of binding RNA polymerase and promoting the transcription of an operably-associated nucleic acid sequence. Such regulatory regions may include those 5'-non-coding sequences involved with initiation of transcription and translation, such as the TATA box, capping sequence, CAAT sequence, and the like. The non-coding region 3' to the coding sequence may contain transcriptional termination regulatory sequences, such as terminators and polyadenylation sites.

Both constitutive and inducible regulatory regions may be used for expression of the modified hsp. It may be desirable to use inducible promoters when the conditions optimal for growth of the recombinant cells and the conditions for high level expression of the modified hsp are different. Examples of useful regulatory regions are provided in the next section below.

In order to attach DNA sequences with regulatory functions, such as promoters, to the modified hsp gene sequence or to insert the modified hsp gene sequence into the cloning site of a vector, linkers or adapters providing the appropriate compatible restriction sites may be ligated to the ends of the cDNAs by techniques well known in the art (Wu et al., 1987, Methods in Enzymol 152:343-349). Cleavage with a restriction enzyme can be followed by modification to create blunt ends by digesting back or filling in single-stranded DNA termini before ligation. Alternatively, a desired restriction enzyme site can be introduced into a fragment of DNA by amplification of the DNA by use of PCR with primers containing the desired restriction enzyme site.

An expression construct comprising a modified hsp sequence operably associated with regulatory regions can be directly introduced into appropriate host cells for expression and production of modified hsp-peptide complexes without further cloning. See, for example, U.S. Pat. No. 5,580,859. The expression constructs can also contain DNA sequences that facilitate integration of the modified hsp sequence into the genome of the host cell, e.g., via homologous recombination. In this instance, it is not necessary to employ an expression vector comprising a replication origin suitable for appropriate host cells in order to propagate and express the modified hsp in the host cells.

5.2.1 Host-Vector Systems

Described herein are systems of vectors and host cells that can be used for the expression of modified hsps. A variety of expression vectors may be used in the present invention which include, but are not limited to, plasmids, cosmids, phage, phagemids, or modified viruses. Typically, such expression vectors comprise a functional origin of replication for propagation of the vector in an appropriate host cell, one or more restriction endonuclease sites for insertion of the modified hsp gene sequence, and one or more selection markers. The expression vector must be used with a compatible host cell which may be derived from a prokaryotic or an eukaryotic organism including but not limited to bacteria, yeasts, insects, mammals, and humans.

Expression constructs and vectors are introduced into host cells for the purpose of producing a secreted modified hsps. Any cell type that can produce heat shock proteins and is compatible with the expression vector may be used, including those that have been cultured in vitro or genetically engineered. Host cells may be obtained from normal or affected subjects, including healthy humans, cancer patients, and patients with an infectious disease, private laboratory deposits, public culture collections such as the American Type Culture Collection, or from commercial suppliers.

Cells into which a modified hsp gene sequence can be introduced for purposes of production and secretion of modified hsp-antigenic peptide complexes in vivo may include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc. The choice of cell type depends on the type of tumor or infectious disease being treated or prevented, and can be determined by one of skill in the art.

Different host cells have characteristic and specific mechanisms for the post-translational processing and modification of proteins. A host cell may be chosen which modifies and processes the expressed gene products in a specific fashion similar to the way the recipient processes its hsps. For the purpose of producing large amounts of hsp, it is preferable that the type of host cell used in the present invention has been used for expression of heterologous genes, and is reasonably well characterized and developed for large-scale production processes. In a specific embodiment, the host cells are from the same patient to whom modified hsp-peptide complexes or recombinant cells secreting modified hsp-peptide complexes are subsequently administered, i.e., the cell used for expression of modified hsp and for administration to a subject is autologous to the subject.

In a particular embodiment, an expression construct comprising a modified hsp gene sequence is introduced into an antigenic cell. As used herein, antigenic cells may include preneoplastic cells that are infected with a cancer-causing infectious agent, such as a virus, but which are not yet neoplastic; or antigenic cells that have been exposed to a mutagen or cancer-causing agent, such as, for example DNA-damaging agents, radiation, etc. Other cells that can be used are preneoplastic cells which are in transition from a normal to a neoplastic form as characterized by morphology, physiological or biochemical functions.

Preferably, the cancer cells and preneoplastic cells used in the methods of the invention are of mammalian origin. Mammals contemplated by this aspect of the invention include humans, companion animals (e.g., dogs and cats), livestock animals (e.g., sheep, cattle, goats, pigs and horses), laboratory animals (e.g., mice, rats and rabbits), and captive or free wild animals.

In various embodiments, any cancer cells, preferably human cancer cells, can be used in the present methods for producing modified hsp-peptide complexes, or for use as a vaccine. The cancer cells provide the antigenic peptides which become associated non-covalently with the expressed modified hsp. Cancers which can be treated or prevented with immunogenic compositions prepared by methods of the invention include, but are not limited to, tumors such as sarcomas and carcinomas. Examples of cancers that are amenable to the methods of the invention are listed in Section 5.7. Accordingly, any tissues or cells isolated from a preneoplastic lesion, a cancer, including cancer that has metastasized to multiple remote sites, can be used in the present method. For example, cells found in abnormally growing tissue, circulating leukemic cells, metastatic lesions as well as solid tumor tissue can be used.

In another embodiment, cell lines derived from a preneoplastic lesion, cancer tissues or cancer cells can also be used, provided that the cells of the cell line have at least one or more antigenic determinants in common with antigens on the target cancer cells. Cancer tissues, cancer cells, cells infected with a cancer-causing agent, other preneoplastic cells, and cell lines of human origin are preferred. Preferably, cancer cells are used that are excised from the patient to which ultimately the complexes are to be administered, i.e., the autologous embodiment of the invention, although this need not be the case (e.g., the cancer cells can be from one or more different individuals).

Cancer and preneoplastic cells can be identified by any method known in the art. For example, cancer cells can be identified by morphology, enzyme assays, proliferation assays, cytogenetic characterization, DNA mapping, DNA sequencing, the presence of cancer-causing virus, or a history of exposure to mutagen or cancer-causing agent, imaging, etc. As for another example, cancer cells can be obtained by surgery, endoscopy, or other biopsy techniques. If some distinctive characteristics of the cancer cells are known, they can also be obtained or purified by any biochemical or immunological methods known in the art, such as but not limited to affinity chromatography, and fluorescence activated cell sorting (e.g., with fluorescently tagged antibody against an antigen expressed by the cancer cells).

There is no requirement that a clonal or homogeneous or purified population of cancer cells be used. Cancer tissues, cancer cells or cell lines may be obtained from a single individual or pooled from several individuals. It is not essential to use cells of the ultimate target in vivo (e.g., cells from the tumor of the intended recipient), so long as at least one or more antigenic determinants on the target cancer cells is present on the cells used for expression of a modified hsp. In addition, cells derived from distant metastases may be used to prepare an immunogenic composition against the primary cancer. A mixture of cells can be used provided that a substantial number of cells in the mixture are cancer cells and share at least one antigenic determinant with the target cancer cell. In a specific embodiment, the cancer cells to be used in expressing a modified hsp are purified.

Vectors based on $E.$ $coli$ are the most popular and versatile systems for high level expression of foreign proteins (Makrides, 1996, Microbiol Rev, 60:512-538). Non-limiting examples of regulatory regions that can be used for expression in $E.$ $coli$ may include but not limited to lac, trp, lpp, phoA, recA, tac, T3, T7 and $\lambda P_L$ (Makrides, 1996, Microbiol Rev, 60:512-538). Non-limiting examples of prokaryotic expression vectors may include the λgt vector series such as λgt11 (Huynh et al., 1984 in "DNA Cloning Techniques", Vol. I: A Practical Approach (D. Glover, ed.), pp. 49-78, IRL Press, Oxford), and the pET vector series (Studier et al., 1990, Methods Enzymol., 185:60-89). However, a potential drawback of a prokaryotic host-vector system is the inability to perform many of the post-translational processing of mammalian cells. Thus, an eukaryotic host-vector system is preferred, a mammalian host-vector system is more preferred, and a human host-vector system is the most preferred.

For expression of modified hsps in mammalian host cells, a variety of regulatory regions can be used, for example, the SV40 early and late promoters, the cytomegalovirus (CMV) immediate early promoter, and the Rous sarcoma virus long terminal repeat (RSV-LTR) promoter. Inducible promoters that may be useful in mammalian cells include but are not limited to those associated with the metallothionein II gene, mouse mammary tumor virus glucocorticoid responsive long terminal repeats (MMTV-LTR), β-interferon gene, and hsp70 gene (Williams et al., 1989, Cancer Res. 49:2735-42; Taylor et al., 1990, Mol. Cell Biol., 10:165-75). It may be advantageous to use heat shock promoters or stress promoters to drive expression of the modified hsp in recombinant host cells.

The following animal regulatory regions, which exhibit tissue specificity and have been utilized in transgenic animals, can also be used in tumor cells of a particular tissue type: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), betaglobin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

The efficiency of expression of the modified hsp in a host cell may be enhanced by the inclusion of appropriate transcription enhancer elements in the expression vector, such as those found in SV40 virus, Hepatitis B virus, cytomegalovirus, immunoglobulin genes, metallothionein, β-actin (see Bittner et al., 1987, Methods in Enzymol. 153:516-544; Gorman, 1990, Curr. Op. in Biotechnol. 1:36-47).

The expression vector may also contain sequences that permit maintenance and replication of the vector in more than one type of host cell, or integration of the vector into the host chromosome. Such sequences may include but are not limited to replication origins, autonomously replicating sequences (ARS), centromere DNA, and telomere DNA. It may also be advantageous to use shuttle vectors which can be replicated and maintained in at least two types of host cells.

In addition, the expression vector may contain selectable or screenable marker genes for initially isolating, identifying or tracking host cells that contain DNA encoding a modified hsp. For long term, high yield production of modified hsp-peptide complexes, stable expression in mammalian cells is preferred. A number of selection systems may be used for mammalian cells, including but not limited to the Herpes simplex virus thymidine kinase (Wigler et al., 1977, Cell 11:223), hypoxanthine-guanine phosphoribosyltransferase (Szybalski and Szybalski, 1962, Proc. Natl. Acad. Sci. USA 48:2026), and adenine phosphoribosyltransferase (Lowy et al., 1980, Cell 22:817) genes can be employed in tk−, hgprt− or aprt− cells, respectively. Also, antimetabolite resistance can be used as the basis of selection for dihydrofolate reductase (dhfr), which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neomycin phosphotransferase (neo), which confers resistance to the aminoglycoside G-418 (Colberre-Garapin et al., 1981, J. Mol. Biol. 150:1); and hygromycin phosphotransferase (hyg), which confers resistance to hygromycin (Santerre et al., 1984, Gene 30:147). Other selectable markers, such as but not limited to histidinol and Zeocin™ can also be used.

Preferred mammalian host cells include but are not limited to those derived from humans, monkeys and rodents, (see, for example, Kriegler M. in "Gene Transfer and Expression: A Laboratory Manual", New York, Freeman & Co. 1990), such as monkey kidney cell line transformed by SV40 (COS-7, ATCC CRL 1651); human embryonic kidney line (293, 293-EBNA, or 293 cells subcloned for growth in suspension culture, Graham et al., J. Gen. Virol., 36:59, 1977; baby hamster kidney cells (BHK, ATCC CCL 10); chinese hamster ovary-cells-DHFR (CHO, Urlaub and Chasin. Proc. Natl. Acad. Sci. 77; 4216, 1980); mouse sertoli cells (Mather, Biol. Reprod. 23:243-251, 1980); mouse fibroblast cells (NIH-3T3), monkey kidney cells (CV1 ATCC CCL 70); african green monkey kidney cells. (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); and mouse mammary tumor cells (MMT 060562, ATCC CCL51). Exemplary cancer cell types used for demonstrating the utility of recombinant cells (producing modified hsp-peptide complexes) as a cancer vaccine are provided as follows: mouse fibroblast cell line, NIH3T3, mouse Lewis lung carcinoma cell line, LLC, mouse mastocytoma cell line, P815, mouse lymphoma cell line, EL4 and its ovalbumin transfectant, E.G7, mouse melanoma cell line, B16F10, mouse fibrosarcoma cell line, MC57, and human small cell lung carcinoma cell lines, SCLC#2 and SCLC#7.

A number of viral-based expression systems may also be utilized with mammalian cells to produce modified hsps. Vectors using DNA virus backbones have been derived from simian virus 40 (SV40) (Hamer et al., 1979, Cell 17:725), adenovirus (Van Doren et al., 1984, Mol Cell Biol 4:1653), adeno-associated virus (McLaughlin et al., 1988, J Virol 62:1963), and bovine papillomas virus (Zinn et al., 1982, Proc Natl Acad Sci 79:4897). In cases where an adenovirus is used as an expression vector, the donor DNA sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing heterologous products in infected hosts. (See e.g., Logan and Shenk, 1984, Proc. Natl. Acad. Sci. (USA) 81:3655-3659).

Bovine papillomavirus (BPV) can infect many higher vertebrates, including man, and its DNA replicates as an episome. A number of shuttle vectors have been developed for recombinant gene expression which exist as stable, multicopy (20-300 copies/cell) extrachromosomal elements in mammalian cells. Typically, these vectors contain a segment of BPV DNA (the entire genome or a 69% transforming fragment), a promoter with a broad host range, a polyadenylation signal, splice signals, a selectable marker, and "poisonless" plasmid sequences that allow the vector to be propagated in E. coli. Following construction and amplification in bacteria, the expression gene construct are transfected into cultured mammalian cells by, for example, the calcium phosphate coprecipitation technique. For those host cells that do not manifest a transformed phenotype, selection of transformants is achieved by use of a dominant selectable marker, such as histidinol and G418 resistance. As described in Section 6, a modified hsp gene sequence was inserted into two BPV vectors, pBCMGSNeo and pBCMGHis (Karasuyama et al., Eur. J. Immunol. 18:97-104; Ohe et al., Human Gene Therapy, 6:325-33) which were then transfected into a diverse range of cell types for expression of the modified hsp.

Alternatively, the vaccinia 7.5K promoter may be used. (See, e.g., Mackett et al., 1982, Proc. Natl. Acad. Sci. (USA) 79:7415-7419; Mackett et al., 1984, J. Virol. 49:857-864; Panicali et al., 1982, Proc. Natl. Acad. Sci. 79:4927-4931.) In cases where a human host cell is used, vectors based on the Epstein-Barr virus (EBV) origin (OriP) and EBV nuclear antigen 1 (EBNA-1; a trans-acting replication factor) can be used. Such vectors can be used with a broad range of human host cells, e.g., EBO-pCD (Spickofsky et al., 1990, DNA Prot Eng Tech 2:14-18); pDR2 and λDR2 (available from Clontech Laboratories).

Modified hsps may also be made with a retrovirus-based expression system. Retroviruses, such as Moloney murine leukemia virus, can be used since most of the viral gene sequence can be removed and replaced with modified hsp gene sequence while the missing viral functions can be supplied in trans. In contrast to transfection, retroviruses can efficiently infect and transfer genes to a wide range of cell types including, for example, primary hematopoietic cells. Moreover, the host range for infection by a retroviral vector can be manipulated by the choice of envelope used for vector packaging.

For example, a retroviral vector can comprise a 5' long terminal repeat (LTR), a 3' LTR, a packaging signal, a bacterial origin of replication, and a selectable marker. The modified hsp DNA is inserted into a position between the 5' LTR and 3' LTR, such that transcription from the 5' LTR promoter transcribes the cloned DNA. The 5' LTR comprises a promoter, including but not limited to an LTR promoter, an R region, a U5 region and a primer binding site, in that order. Nucleotide sequences of these LTR elements are well known in the art. A heterologous promoter as well as multiple drug selection markers may also be included in the expression vector to facilitate selection of infected cells. See, McLauchlin et al., 1990, Prog Nucleic Acid Res and Molec Biol 38:91-135; Morgenstern et al., 1990, Nucleic Acid Res 18:3587-3596; Choulika et al., 1996, J Virol 70:1792-1798; Boesen et al., 1994, Biotherapy 6:291-302; Salmons and Gunzberg, 1993, Human Gene Therapy 4:129-141; and Grossman and Wilson, 1993, Curr. Opin. in Genetics and Devel. 3:110-114.

Other useful eukaryotic host-vector system may include yeast and insect systems. In yeast, a number of vectors containing constitutive or inducible promoters may be used with *Saccharomyces cerevisiae* (baker's yeast), *Schizosaccharomyces pombe* (fission yeast), *Pichia pastoris*, and *Hansenula polymorpha* (methylotropic yeasts). For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces*, 1982, Eds. Strathern et al., Cold Spring Harbor Press, Vols. I and II.

In an insect system, *Autographa californica* nuclear polyhidrosis virus (AcNPV) a baculovirus, can be used as a vector to express modified hsp in *Spodoptera frugiperda* cells. The modified hsp gene sequences may be cloned into non-essential regions (for example the polyhedrin gene) of the virus and placed under control of an AcNPV promoter (for example the polyhedrin promoter). These recombinant viruses are then used to infect host cells in which the inserted DNA is expressed. (See e.g., Smith et al., 1983, J Virol 46:584; Smith, U.S. Pat. No. 4,215,051.)

Any of the cloning and expression vectors described herein may be synthesized and assembled from known DNA sequences by well known techniques in the art. The regulatory regions and enhancer elements can be of a variety of origins, both natural and synthetic. Some vectors and host cells may be obtained commercially. Non-limiting examples of useful vectors are described in Appendix 5 of Current Protocols in Molecular Biology, 1988, ed. Ausubel et al., Greene Publish. Assoc. & Wiley Interscience, which is incorporated herein by reference; and the catalogs of commercial suppliers such as Clontech Laboratories, Stratagene Inc., and Invitrogen, Inc.

5.2.2. Expression of Modified Hsps

Expression constructs containing cloned nucleotide sequence encoding modified hsps can be introduced into the host cell by a variety of techniques known in the art, including but not limited to, for prokaryotic cells, bacterial transformation (Hanahan, 1985, in DNA Cloning, A Practical Approach, 1:109-136), and for eukaryotic cells, calcium phosphate mediated transfection (Wigler et al., 1977, Cell 11:223-232), liposome-mediated transfection (Schaefer-Ridder et al., 1982, Science 215:166-168), electroporation (Wolff et al., 1987, Proc Natl Acad Sci 84:3344), and microinjection (Cappechi, 1980, Cell 22:479-488). Co-expression of a modified hsp and an antigen in the same host cell can be achieved by essentially the same methods.

For long term, high yield production of properly processed modified hsp or modified hsp-peptide complexes, stable expression in mammalian cells is preferred. Cell lines that stably express modified hsp or modified hsp-peptide complexes may be engineered by using a vector that contains a selectable marker. By way of example but not limitation, following the introduction of the expression constructs, engineered cells may be allowed to grow for 1-2 days in an enriched media, and then are switched to a selective media. The selectable marker in the expression construct confers resistance to the selection and optimally allows cells to stably integrate the expression construct into their chromosomes and to grow in culture and to be expanded into cell lines. Such cells can be cultured for a long period of time while modified hsp is expressed continuously.

The recombinant cells may be cultured under standard conditions of temperature, incubation time, optical density, and media composition. Alternatively, a recombinant antigenic cells may be cultured under conditions emulating the nutritional and physiological requirements of the cancer cell or infected cell. However, conditions for growth of recombinant cells may be different from those for expression of modified hsps and antigenic proteins. Modified culture conditions and media may also be used to enhance production of hsp-peptide complexes. For example, recombinant cells containing modified hsps with their cognate promoters may be exposed to heat or other environmental stress, or chemical stress. Any techniques known in the art may be applied to establish the optimal conditions for producing modified hsp or modified hsp-peptide complexes.

In an embodiment where the recombinant cells expressing the modified hsp is used as a vaccine, the modified hsp gene sequence is introduced into a cell prior to administration in vivo of the resulting recombinant cell. Such introduction can be carried out by any method known in the art, including gene therapy art, such as but not limited to transfection, electroporation, microinjection, infection with a viral or bacteriophage vector containing the modified hsp gene sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, Meth. Enzymol. 217:599-618; Cohen et al., 1993, Meth. Enzymol. 217:618-644; Cline, 1985, Pharmac. Ther. 29:69-92) may be used in accordance with the present invention, provided that the necessary developmental and physiological functions of the recipient cells are not disrupted. The technique should provide for the stable transfer of the modified hsp gene sequence to the cell, so that the sequence is expressible by the cell and preferably heritable and expressible by its cell progeny.

The resulting recombinant cells can be delivered to a patient by various methods known in the art. In a preferred embodiment, epithelial cells are injected, e.g., subcutaneously. In another embodiment, recombinant skin cells may be applied as a skin graft onto the patient. Recombinant blood cells (e.g., hematopoietic stem or progenitor cells) are preferably administered intravenously. The amount of cells envisioned for use depends on the desired effect, patient state, etc., and can be determined by one skilled in the art.

5.2.3. Co-expression of Modified Hsps and Antigens

In an alternative embodiment, an expressible form of a nucleotide sequence encoding a protein antigen or portions thereof can be introduced into a recombinant cell containing a expressible modified hsp gene sequence so that the antigen is co-expressed with a modified hsp. Methods for obtaining the nucleotide sequence encoding an antigen are described in Section 5.4.5. Any techniques for introduction of the expressible form of the antigen gene sequence, such as not limited to those described in Section 5.2.2, can be used. The protein antigen or portions thereof becomes non-covalently associated with the modified hsp in the ER of the recombinant cell, and the resulting modified hsp-antigenic peptide complex is secreted. Such a complex can be purified from the cell culture media by any of the methods described in Section 5.3, and other methods known in the art. The purified modified hsp-antigen complex can be used as a vaccine to stimulate an immune response against the antigenic protein in a subject for the purpose of treatment or prevention of cancer or infectious diseases.

Further, the recombinant cells containing expressible forms of both a modified hsp gene sequence and a nucleotide sequence encoding an antigenic protein can be used directly as a vaccine for injection into a subject. As described above, such cells secrete modified hsp-antigen complex which can stimulate an immune response against the antigenic protein in the subject for the purpose of treatment or prevention of cancer or infectious diseases.

The uses of such modified hsp-peptide complex and recombinant cells containing expressible forms of a modified hsp and an antigen gene sequence to treat or prevent cancer or infectious diseases are described in Sections 5.7 and 5.8.

5.3. Purification of Modified Hsp-Peptide Complexes

Generally, the modified hsp of the invention can be recovered and purified from recombinant cell cultures by known methods, including ammonium sulfate precipitation, acid extraction, anion or cation exchange chromatography, phosphocellulose chromatography, immunoaffinity chromatography, hydroxyapatite chromatography, and lectin chromatography.

The purification of hsp70-peptide complexes from cell lysates has been described previously, see, for example, Udono et al., 19.93, J. Exp. Med. 178:1391-1396. The purification of hsp90-peptide complexes and gp96-peptide complexes from cell lysates have been described, for example, in WO 95/24923, dated Sep. 21, 1995, and WO 97/10000, dated Mar. 20, 1997. These methods can be used to purify the modified hsp or modified hsp-peptide complexes of the invention from the recombinant cells, and with minor modifications known in the art, the modified hsp or modified hsp-peptide complexes from the cell culture.

However, the invention provides improved methods for purification of the modified hsps which are based on the properties of the peptide tag present on the modified hsp. One approach is based on specific molecular interactions between a tag and its binding partner. The other approach relies on the immunospecific binding of an antibody to an epitope present on the tag. The principle of affinity chromatography well known in the art is generally applicable to both of these approaches.

Described below are several methods based on specific molecular interactions of a tag and its binding partner.

A method that is generally applicable to purifying modified hsps that are fused to the constant regions of immunoglobulin is protein A affinity chromatography, a technique that is well known in the art. *Staphylococcus* protein A is a 42 kD polypeptide that binds specifically to a region located between the second and third constant regions of heavy chain immunoglobulins. Because of the Fc domains of different classes, subclasses and species of immunoglobulins, affinity of protein A for human Fc regions is strong, but may vary with other species. Subclasses that are less preferred include human IgG-3, and most rat subclasses. For certain subclasses, protein G (of Streptococci) may be used in place of protein A in the purification. Protein-A sepharose (Pharmacia or Biorad) is a commonly used solid phase for affinity purification of antibodies, and can be used essentially in the same manner for the purification of modified hsp fused to an immunoglobulin Fc fragment. Secreted modified hsp present in cell supernatant binds specifically to protein A on the solid phase, while the contaminants are washed away. Bound modified hsp can be eluted by various buffer systems known in the art, including a succession of citrate, acetate and glycine-HCl buffers which gradually lowers the pH. This method is less preferred if the recombinant cells also produce antibodies which will be copurified with the modified hsp. See, for example, Langone, 1982, J. Immunol. meth. 51:3; Wilchek et al., 1982, Biochem. Intl. 4:629; Sjobring et al., 1991, J. Biol. Chem. 26:399; page 617-618, in Antibodies A Laboratory Manual, edited by Harlow and Lane, Cold Spring Harbor laboratory, 1988.

Alternatively, a polyhistidine tag may be used, in which case, the modified hsp can be purified by metal chelate chromatography. The polyhistidine tag, usually a sequence of six histidines, has a high affinity for divalent metal ions, such as nickel ions ($Ni^{2+}$), which can be immobilized on a solid phase, such as nitrilotriacetic acid-matrices. Polyhistidine has a well characterized affinity for $Ni^{2+}$-NTA-agarose, and can be eluted with either of two mild treatments: imidazole (0.1-0.2 M) will effectively compete with the resin for binding sites; or lowering the pH just below 6.0 will protonate the histidine sidechains and disrupt the binding. The purification method comprises loading the cell culture supernatant onto the $Ni^{2+}$-NTA-agarose column, washing the contaminants through, and eluting the modified hsp with imidazole or weak acid. Ni$^{2+}$-NTA-agarose can be obtained from commercial suppliers such as Sigma (St. Louis) and Qiagen. Antibodies that recognize the polyhistidine tag are also available which can be used to detect and quantitate the modified hsp.

Another exemplary peptide tag that can be used is the glutathione-S-transferase (GST) sequence, originally cloned from the helminth, *Schistosoma japonicum*. In general, a modified hsp-GST fusion expressed in a prokaryotic host cell, such as *E. coli*, can be purified from the cell culture supernatant by absorption with glutathione agarose beads, followed by elution in the presence of free reduced glutathione at neutral pH. Denaturing conditions are not required at any stage during purification, and therefore, it may be desirable for use in the loading of immobilized modified hsp with antigenic peptides. Moreover, since GST is known to form dimers under certain conditions, dimeric modified hsp may be obtained. See, Smith, 1993, Methods Mol. Cell Bio. 4:220-229.

Another useful peptide tag that can be used is the maltose binding protein (MBP) of *E. coli*, which is encoded by the malE gene. The secreted modified hsp-MBP present in the cell supernatant binds to amylose resin while contaminants are washed away. The bound modified hsp-MBP is eluted from the amylose resin by maltose. See, for example, Guan et al., 1987, Gene 67:21-30.

The second approach for purifying modified hsp is applicable to peptide tags that contain an epitope for which polyclonal or monoclonal antibodies are available. Various methods known in the art for purification of protein by immunospecific binding, such as immunoaffinity chromatography, and immunoprecipitation, can be used. See, for example, Chapter 13 in Antibodies A Laboratory Manual, edited by Harlow and Lane, Cold Spring Harbor laboratory, 1988; and Chapter 8, Sections I and II, in Current Protocols in Immunology, ed. by Coligan et al., John Wiley, 1991; the disclosure of which are both incorporated by reference herein.

The embodiments described above may be used to recover and purify secreted modified hsp-peptide complexes from the cell culture medium of mammalian cells, such as, human cells, expressing a modified hsp of the invention. The methods can be adapted to perform medium and large scale purification of modified hsp and/or modified hsp-peptide complex. Methods that do not require lowering pH or denaturing conditions are most preferred for purification of modified hsp-peptide complexes. Although described for tumor cells in the Examples, the methods described may be used to isolate hsps from any eukaryotic cells, for example, tissues, isolated cells, or immortalized eukaryote cell lines infected with an intracellular pathogen, or cells obtained from a subject infected with a pathogen.

5.4 In Vitro Production of Hsp-Antigenic Molecule Complexes

In an embodiment in which complexes of modified hsps and the peptides with which they are endogenously associated in the recombinant cells are not employed, complexes of modified hsps to antigenic molecules are produced in vitro. As will be appreciated by those skilled in the art, the antigenic peptides either isolated by the procedures described below or chemically synthesized or recombinantly produced may be reconstituted with a variety of modified heat shock proteins in vitro to generate immunogenic non-covalent modified hsp-peptide complexes. Such complexes can be used for the immunotherapeutic or prophylactic vaccines of the invention.

The methods of in vitro production of modified hsp-peptide complex can be adapted to be carried out on a medium scale or a large scale.

Antigens or antigenic portions thereof, that are specific to one or more types of cancer cells, or that are specific to an infected cell or an infectious agent, can be selected for use as antigenic peptides, for complexing to modified hsps, from among those known in the art or determined by immunoassay to be able to bind to antibody or MHC molecules (antigenicity) or generate immune response (immunogenicity).

5.4.1 Exogenous Antigenic Molecules

To determine immunogenicity or antigenicity of a putative antigen by detecting binding to antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in vivo immunoassays (using colloidal gold, enzyme or radioisotope labels, for example), western blots, immunoprecipitation reactions, agglutination assays (e.g., gel agglutination assays, hemagglutination assays), complement fixation assays, immunofluorescence assays, protein A assays, and immunoelectrophoresis assays, etc. In one aspect, antibody binding is detected by detecting a label on the primary antibody. In another aspect, the primary antibody is detected by detecting binding of a secondary antibody or reagent to the primary antibody. In a further aspect, the secondary antibody is labelled. Many means are known in the art for detecting binding in an immunoassay and are envisioned for use. In one embodiment for detecting immunogenicity, T cell-mediated responses can be assayed by standard methods, e.g., in vitro cytoxicity assays or in vivo delayed-type hypersensitivity assays.

Potentially useful antigens or derivatives thereof for use as antigenic molecules can also be identified by various criteria, such as the antigen's involvement in neutralization of a pathogen's infectivity (wherein it is desired to treat or prevent infection by such a pathogen) (Norrby, 1985, Summary, in Vaccines 85, Lerner, et al. (eds.), Cold Spring Harbor Laboratory, Cold Spring Harbor, N.Y., pp. 388-389), type or group specificity, recognition by patients' antisera or immune cells, and/or the demonstration of protective effects of antisera or immune cells specific for the antigen. In addition, where it is desired to treat or prevent a disease caused by pathogen, the antigen's encoded epitope should preferably display a small or no degree of antigenic variation in time or amongst different isolates of the same pathogen.

Preferably, where it is desired to treat or prevent cancer, known tumor-specific antigens or fragments or derivatives thereof are used. For example, such tumor specific or tumor-associated antigens include but are not limited to KS 1/4 pan-carcinoma antigen (Perez and Walker, 1990, J. Immunol. 142:3662-3667; Bumal, 1988, Hybridoma 7(4):407-415); ovarian carcinoma antigen (CA125) (Yu, et al., 1991, Cancer Res. 51(2):468-475); prostatic acid phosphate (Tailer, et al., 1990, Nucl. Acids Res. 18(16):4928); prostate specific antigen (Henttu and Vihko, 1989, Biochem. Biophys. Res. Comm. 160(2):903-910; Israeli, et al., 1993, Cancer Res. 53:227-230); melanoma-associated antigen p97 (Estin, et al., 1989, J. Natl. Cancer Inst. 81(6):445-446); melanoma antigen gp75 (Vijayasardahl, et al., 1990, J. Exp. Med. 171(4):1375-1380); high molecular weight melanoma antigen (Natali, et al., 1987, Cancer 59:55-63) and prostate specific membrane antigen.

In a specific embodiment, an antigen or fragment or derivative thereof specific to a certain tumor is selected for complexing to modified hsp and subsequent administration to a patient having that tumor.

Preferably, where it is desired to treat or prevent viral diseases, molecules comprising epitopes of known viruses are used. For example, such antigenic epitopes may be prepared from viruses including, but not limited to, hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, human immunodeficiency virus type I (HIV-I), and human immunodeficiency virus type II (HIV-II).

Preferably, where it is desired to treat or prevent bacterial infections, molecules comprising epitopes of known bacteria are used. For example, such antigenic epitopes may be prepared from bacteria including, but not limited to, *mycobacteria rickettsia, mycoplasma, neisseria* and *legionella*.

Preferably, where it is desired to treat or prevent protozoal infections, molecules comprising epitopes of known protozoa are used. For example, such antigenic epitopes may be prepared from protozoa including, but not limited to, *leishmania, kokzidioa*, and *trypanosoma*.

Preferably, where it is desired to treat or prevent parasitic infections, molecules comprising epitopes of known parasites are used. For example, such antigenic epitopes may be from parasites including, but not limited to, *chlamydia* and *rickettsia*.

5.4.2 Peptides from Hsp-Peptide Complexes

Antigenic peptides for complexing in vitro to modified hsp of the invention can also be obtained from endogenous complexes of peptides and hsps. Two methods may be used to elute the peptide from a hsp-peptide complex. One approach involves incubating the hsp-peptide complex in the presence of ATP. The other approach involves incubating the complexes in a low pH buffer.

Briefly the complex of interest is centrifuged through a Centricon 10 assembly (Millipore) to remove any low molecular weight material loosely associated with the complex. The large molecular weight fraction may be removed and analyzed by SDS-PAGE while the low molecular weight may be analyzed by HPLC as described below. In the ATP incubation protocol, the hsp-peptide complex in the large molecular weight fraction is incubated with 10 mM ATP for 30 minutes at room temperature. In the low pH protocol, acetic acid or trifluoroacetic acid (TFA) is added to the hsp-peptide complex to give a final concentration of 10% (vol/vol) and the mixture incubated at room temperature or in a boiling water bath or any temperature in between, for 10 minutes (See, Van Bleek, et al., 1990, Nature 348:213-216; and Li, et al., 1993, EMBO Journal 12:3143-3151).

The resulting samples are centrifuged through a Centricon 10 assembly as mentioned previously. The high and low molecular weight fractions are recovered. The remaining large molecular weight hsp-peptide complexes can be reincubated with ATP or low pH to remove any remaining peptides.

The resulting lower molecular weight fractions are pooled, concentrated by evaporation and dissolved in 0.1% TFA. The dissolved material is then fractionated by reverse phase high pressure liquid chromatography (HPLC) using for example a VYDAC C18 reverse phase column equilibrated with 0.1% TFA. The bound material is then eluted at a flow rate of about 0.8 ml/min by developing the column with a linear gradient of 0 to 80% acetonitrile in 0.1% TFA. The elution of the peptides can be monitored by $OD_{210}$ and the fractions containing the peptides collected.

5.4.3 Peptides from MHC-Peptide Complexes

Peptides bound to MHC molecules can also be used to form complexes with modified hsps of the invention in vitro. The isolation of potentially immunogenic peptides from MHC molecules is well known in the art and so is not described in detail herein (See, Falk, et al., 1990, Nature 348:248-251; Rotzsche, at al., 1990, Nature 348:252-254; Elliott, et al., 1990, Nature 348:191-197; Falk, et al., 1991, Nature 351: 290-296; Demotz, et al., 1989, Nature 343:682-684; Rotzsche, et al., 1990, Science 249:283-287), the disclosures of which are incorporated herein by reference.

Briefly, MHC-peptide complexes may be isolated by a conventional immunoaffinity procedure. The peptides then may be eluted from the MHC-peptide complex by incubating the complexes in the presence of about 0.1% TFA in acetonitrile. The eluted peptides may be fractionated and purified by reverse phase HPLC, as before.

5.4.4 Synthetic Peptides

The amino acid sequences of the peptides eluted from MHC molecules or hsps may be determined either by manual or automated amino acid sequencing techniques well known in the art. Once the amino acid sequence of a potentially protective peptide has been determined, the peptide may be synthesized in any desired amount using conventional peptide synthesis or other protocols well known in the art.

Peptides having the same amino acid sequence as those isolated above may be synthesized by solid-phase peptide synthesis using procedures similar to those described by Merrifield, 1963, J. Am. Chem. Soc., 85:2149. During synthesis, N-α-protected amino acids having protected side chains are added stepwise to a growing polypeptide chain linked by its C-terminal and to an insoluble polymeric support i.e., polystyrene beads. The peptides are synthesized by linking an amino group of an N-α-deprotected amino acid to an α-carboxyl group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc which is acid labile and Fmoc which is base labile. Details of appropriate chemistries, resins, protecting groups, protected amino acids and reagents are well known in the art and so are not discussed in detail herein (See, Atherton, et al., 1989, Solid Phase Peptide Synthesis: A Practical Approach, IRL Press, and Bodanszky, 1993, Peptide Chemistry, A Practical Textbook, 2nd Ed., Springer-Verlag).

Purification of the resulting peptides is accomplished using conventional procedures, such as preparative HPLC using gel permeation, partition and/or ion exchange chromatography. The choice of appropriate matrices and buffers are well known in the art and so are not described in detail herein.

5.4.5 Genetic Sequences Encoding Antigens

In a particular embodiment of the invention, a nucleotide sequence encoding a protein antigen or portions thereof can be introduced into a host cell for production of the antigen. The nucleotide sequence encoding any antigenic protein can be obtained and cloned into an expression vector for expression essentially by the same methods described for the cloning and expression of a hsp gene sequence. The techniques are described in Sections 5.1-5.1.1 and 5.2-5.2.2 and well known in the art. The recombinant antigenic protein or portions thereof can be purified by any methods appropriate for the protein, and then used to form complexes with modified hsps in vitro as described in Section 5.4.6. Such a modified hsp-antigen complex can be used as a vaccine to stimulate an immune response against the antigenic protein in a subject for the purpose of treatment or prevention of cancer or infectious diseases.

5.4.6 Formation of Modified Hsp-Peptide Complexes In Vitro

A preferred, exemplary protocol for noncovalently complexing a modified hsp and an antigenic molecule in vitro is provided below. It may be advantageous to use modified hsps that are reversibly bound to a solid phase by their peptide tag to facilitate buffer exchange, washings and isolation of the complexes before or after the complexing reaction.

Prior to complexing, the modified hsps are pretreated with ATP or low pH to remove any peptides that may be associated with the hsp of interest. When the ATP procedure is used, excess ATP is removed from the preparation by the addition of apyranase as described by Levy et al., 1991, Cell 67:265-274. When the low pH procedure is used, the buffer is readjusted to neutral pH by the addition of pH modifying reagents.

The antigenic molecules (1 μg) and the pretreated modified hsp (9 μg) are admixed to give an approximately 5 antigenic molecule: 1 hsp molar ratio. Then, the mixture is incubated for 15 minutes to 3 hours at 40° to 45° C. in a suitable binding buffer such as one containing 20 mM sodium phosphate, pH 7.2, 350 mM NaCl, 3 mM $MgCl_2$ and 1 mM phenyl methyl sulfonyl fluoride (PMSF). The preparations are centrifuged through a Centricon 10 assembly (Millipore) to remove any unbound peptide. If the modified hsp is bound to a solid phase, the modified hsp-peptide complexes formed can be washed free of unbounded peptide prior to eluting the modified hsp-peptide complex off the solid phase. The association of the peptides with the modified hsp can be assayed by SDS-PAGE. This is the preferred method for in vitro complexing of peptides isolated from MHC-peptide complexes of peptides disassociated from endogenous hsp-peptide complexes.

In an alternative embodiment of the invention, preferred for producing complexes of modified hsp70 to exogenous antigenic molecules such as proteins, 5-10 micrograms of purified hsp is incubated with equimolar quantities of the antigenic molecule in 20 mM sodium phosphate buffer pH 7.5, 0.5M NaCl, 3 mM $MgCl_2$ and 1 mM ADP in a volume of 100 microliter at 37° C. for 1 hr. This incubation mixture is further diluted to 1 ml in phosphate-buffered saline.

In another alternative embodiment of the invention, preferred for producing complexes of modified gp96 to peptides, 5-10 micrograms of modified gp96 immobilized by its affinity tag to a solid phase is incubated with equimolar or excess quantities of the antigenic peptide in a suitable buffer, such as one containing 20 mM sodium phosphate buffer pH 7.5, 0.5M NaCl, 3 nM $MgCl_2$ at about 50° C. for about 10 minutes. For example, modified gp96 containing the Ig tag can be immobilized to protein A-Sepharose for this procedure. This incubation mixture is then further incubated for about 30 minutes at room temperature. The solid phase with the bound modified hsp-peptide complexes is washed several times to remove any unbound peptide. The modified hsp-peptide complexes is then eluted from the solid phase by the appropriate technique.

Following complexing, the immunogenic hsp-antigenic molecule complexes can optionally be assayed in vitro using, for example, the mixed lymphocyte target cell assay (MLTC) described below. Once immunogenic complexes have been isolated they can be optionally characterized further in animal models using the preferred administration protocols and excipients discussed below.

5.5. Determination of Immunogenicity of Hsp-Peptide Complexes

In an optional procedure, the purified modified hsp-peptide complexes can be assayed for immunogenicity using the mixed lymphocyte target culture assay (MLTC) well known in the art.

By way of example but not limitation, the following procedure can be used. Briefly, mice are injected subcutaneously with the candidate modified hsp-peptide complexes. Other mice are injected with either other hsp-peptide complexes from normal, non-recombinant cells or whole infected cells which act as positive controls for the assay. The mice are injected twice, 7-10 days apart. Ten days after the last immunization, the spleens are removed and the lymphocytes released. The released lymphocytes may be restimulated subsequently in vitro by the addition of dead cells that expressed the complex of interest.

For example, $8 \times 10^6$ immune spleen cells may be stimulated with $4 \times 10^4$ mitomycin C treated or γ-irradiated (5-10,000 rads) pathogen-infected cells (or cells transfected with a gene encoding an antigen of the infectious agent, as the case may be), or tumor cells in 3 ml RPMI medium containing 10% fetal calf serum. In certain cases 33% secondary mixed lymphocyte culture supernatant or interleukin 2 (IL-2) may be included in the culture medium as a source of T cell growth factors (See, Glasebrook et al., 1980, J. Exp. Med. 151:876). To test the primary cytotoxic T cell response after immunization, spleen cells may be cultured without stimulation. In some experiments spleen cells of the immunized mice may also be restimulated with antigenically distinct cells, to determine the specificity of the cytotoxic T cell response.

Six days later the cultures are tested for cytotoxicity in a 4 hour $^{51}$Cr-release assay (See, Palladino et al., 1987, Cancer Res. 47:5074-5079 and Blachere, at al., 1993, J. Immunotherapy 14:352-356). In this assay, the mixed lymphocyte culture is added to a target cell suspension to give different effector:target (E:T) ratios (usually 1:1 to 40:1). The target cells are prelabelled by incubating $1 \times 10^6$ target cells in culture medium containing 200 mCi $^{51}$Cr/ml for one hour at 37° C. The cells are washed three times following labeling. Each assay point (E:T ratio) is performed in triplicate and the appropriate controls incorporated to measure spontaneous $^{51}$Cr release (no lymphocytes added to assay) and 100% release (cells lysed with detergent). After incubating the cell mixtures for 4 hours, the cells are pelleted by centrifugation at 200 g for 5 minutes. The amount of $^{51}$Cr released into the supernatant is measured by a gamma counter. The percent cytotoxicity is measured as cpm in the test sample minus spontaneously released cpm divided by the total detergent released cpm minus spontaneously released cpm.

In order to block the MHC class I cascade a concentrated hybridoma supernatant derived from K-44 hybridoma cells (an anti-MHC class I hybridoma) is added to the test samples to a final concentration of 12.5% (Heike et al., 1994, J. Immunotherapy 15:165-174).

An alternative to the chromium-release assay is the ELISPOT assay which measures cytokine release by cytotoxic T cells in vitro after stimulation with specific antigen. Cytokine release is detected by antibodies which are specific for a particular cytokine, such as interleukin-2, tumor necrosis factor α or interferon-γ (for example, see Scheibenbogeh et al., 1997, Int. J. Cancer, 71:932-936). The assay is carried out in a microtitre plate which has been pre-coated with an antibody specific for a cytokine of interest which captures the cytokine secreted by T cells. After incubation of T cells for 24-48 hours in the coated wells, the cytotoxic T cells are removed and replaced with a second labelled antibody that recognizes a different epitope on the cytokine. After extensive washing to remove unbound antibody, an enzyme substrate which produces a colored reaction product is added to the plate. The number of cytokine-producing cells is counted under a microscope. This method has the advantages of short assay time, and sensitivity without the need of a large number of cytotoxic T cells.

5.6. Formulation

Noncovalent complexes of modified hsps and antigenic proteins or peptides purified by the methods of the invention may be formulated into pharmaceutical preparations for administration to mammals for treatment or prevention of cancer or infectious diseases. Drug solubility and the site of absorption are factors which should be considered when choosing the route of administration of a therapeutic agent. Modified hsp-antigenic molecule complexes of the invention may be administered using any desired route of administration, including but not limited to, e.g., subcutaneously, intravenously or intramuscularly, although intradermally or mucosally is preferred. Advantages of intradermal or mucosal administration include use of lower doses and rapid absorption, respectively. Mucosal routes of administration include, but are not limited to, oral, rectal and nasal administration. Preparations for mucosal administrations are suitable in various formulations as described below. The route of administration can be varied during a course of treatment. Preferred dosages, routes of administration and therapeutic regimens for complexes of peptides and naturally occurring hsps are described in PCT International patent applications published as WO 96/10411 and WO 97/10001, which are incorporated by reference herein in their entireties.

In preferred aspects, an amount of modified gp96-peptide complex is administered to a human that is in the range of about 10 to 600 µg, preferably 10 to 100 µg, most preferably about 25 µg, given once weekly for about 4-6 weeks, intradermally with the site of administration varied sequentially.

Compositions comprising noncovalent complexes formulated in a compatible pharmaceutical carrier may be prepared, packaged, and labelled for treatment of the indicated tumor, such as human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease, etc.

If the complex is water-soluble, then it may be formulated in an appropriate buffer, for example, phosphate buffered saline or other physiologically compatible solutions.

Alternatively, if the resulting complex has poor solubility in aqueous solvents, then it may be formulated with a non-ionic surfactant such as Tween, or polyethylene glycol. Thus, the noncovalent complexes and their physiologically acceptable solvates may be formulated for administration by inhalation or insufflation (either through the mouth or the nose) or oral, buccal, parenteral, rectal administration or, in the case of tumors, directly injected into a solid tumor.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

Preparations for oral administration may be suitably formulated to give controlled release of the complexes. Such compositions may take the form of tablets or lozenges formulated in conventional manner.

For administration by inhalation, the complexes may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the complexes and a suitable powder base such as lactose or starch.

The complexes may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The complexes may also be formulated in rectal compositions such as suppositories or retention enemas, e.g., containing conventional suppository bases such as cocoa butter or other glycerides.

In addition to the formulations described previously, the complexes may also be formulated as a depot preparation. Such long acting formulations may be administered by implantation (for example, subcutaneously or intramuscularly) or by intramuscular injection. Thus, for example, the complexes may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

The complexes may, if desired, be presented in a pack or dispenser device which may contain one or more unit dosage forms containing the noncovalent complexes. The pack may for example comprise metal or plastic foil, such as a blister pack. The pack or dispenser device may be accompanied by instructions for administration.

The invention also provides kits for carrying out the therapeutic regimens of the invention. Such kits comprise in one or more containers therapeutically or prophylactically effective amounts of the noncovalent modified hsp-peptide complexes in pharmaceutically acceptable form. The modified hsp-peptide complexes in a vial of a kit of the invention may be in the form of a pharmaceutically acceptable solution, e.g., in combination with sterile saline, dextrose solution, or buffered solution, or other pharmaceutically acceptable sterile fluid. Alternatively, the complex may be lyophilized or desiccated; in this instance, the kit optionally further comprises in a container a pharmaceutically acceptable solution (e.g., saline, dextrose solution, etc.), preferably sterile, to reconstitute the complex to form a solution for injection purposes.

In another embodiment, a kit of the invention further comprises a needle or syringe, preferably packaged in sterile form, for injecting the complex, and/or a packaged alcohol pad. Instructions are optionally included for administration of modified hsp-peptide complexes by a clinician or by the patient.

5.7. Prevention and Treatment of Cancer

There are many reasons why immunotherapy as provided by the noncovalent modified hsp-peptide complexes or recombinant cells expressing modified hsps prepared by the present invention is desired for use in cancer patients. First, if cancer patients are immunosuppressed, and surgery with anesthesia, and subsequent chemotherapy, may worsen the immunosuppression, then with appropriate immunotherapy in the preoperative period, this immunosuppression may be prevented or reversed. This could lead to fewer infectious complications and to accelerated wound healing. Second, tumor bulk is minimal following surgery and immunotherapy is most likely to be effective in this situation. A third reason is the possibility that tumor cells are shed into the circulation at surgery and effective immunotherapy applied at this time can eliminate these cells.

In a specific embodiment, the preventive and therapeutic utility of the invention is directed at enhancing the immunocompetence of the cancer patient either before surgery, at or after surgery, and at inducing tumor-specific immunity to cancer cells, with the objective being inhibition of cancer, and with the ultimate clinical objective being total cancer regression and eradication.

According to the invention, preferred methods of treatment or prevention of cancer comprise isolating cancer cells from one or more individual, preferably the individual in need of treatment, and introducing into such cells an expressible modified hsp gene sequences, preferably as an expression gene construct. The modified hsp gene sequence is manipulated by methods described above in section 5.1, such that the modified hsp gene sequence, in the form of an expression construct, or intrachromosomally integrated, are suitable for expression of the modified hsp in the recombinant cells. The recombinant cells containing the expression gene constructs are cultured under conditions such that modified hsps encoded by the expression gene construct are expressed by the recombinant host cells. Complexes of modified heat shock protein noncovalently associated with peptides of the cancer cell are secreted, and preferably purified from the culture medium by the methods described in section 5.2. Depending on the route of administration, the modified hsp-peptide complexes are formulated accordingly as described in section 5.4, and administered to the individual autologously (e.g., to treat the primary cancer or metastases thereof), or to other individuals who are in need of treatment for cancer of a similar tissue type, or to individuals at enhanced risk of cancer due to familial history or environmental risk factors. Exemplary methods of therapeutic and prophylactic uses of hsp-peptide complexes have also been described in PCT Publications WO 96/10411, dated Apr. 11, 1996, and WO 97/10001, dated Mar. 20, 1997.

For example, treatment with modified hsp-peptide complexes prepared as described above may be started any time after surgery. However, if the patient has received chemotherapy, hsp-antigen complexes are usually administered after an interval of four weeks or more so as to allow the immune system to recover. The therapeutic regimen may include weekly injections of the modified hsp-antigen complex, dissolved in saline or other physiologically compatible solution. The route and site of injection is varied each time, for example, the first injection is given subcutaneously on the left arm, the second injection on the right arm, the third injection on the left abdominal region, the fourth injection on the right abdominal region, the fifth injection on the left thigh, the sixth injection on the right thigh, etc. The same site is repeated after a gap of one or more injections. In addition, injections are split and each half of the dose is administered at a different site on the same day. Overall, the first four to six injections are given at weekly intervals. Subsequently, two injections are given at two-week intervals, followed by a regimen of injections at monthly intervals.

Alternatively, recombinant tumor cells secreting modified hsp-peptide complexes can be used as a vaccine for injection into a patient to stimulate an immune response against the tumor cells or cells bearing tumor antigens. Autologous recombinant tumor cells stably expressing and secreting modified hsp-peptide complexes are preferred. To determine the appropriate dose, the amount of modified hsp-peptide complex secreted by the recombinant cells is quantitated, and the number of recombinant cells used for vaccination is adjusted accordingly to assure a consistent level of secretion in vivo. A preferred dose is the number of recombinant cells that can secrete about 100 ng modified gp96 per 24 hours. For the safety of the patient, the recombinant tumor cells can be irradiated (12000 rad) immediately prior to injection into a patient. Irradiated cells do not proliferate, and can continue to secrete modified hsp-peptide complexes for about 7-10 days which is sufficient to induce an immune response.

Cancers that can be treated or prevented by using noncovalent hsp-peptide complexes prepared by the methods of the present invention include, but not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease. Specific examples of such cancers are described in the sections below.

In a specific embodiment, the cancer is metastatic. In another specific embodiment, the patient having a cancer is immunosuppressed by reason of having undergone anti-cancer therapy (e.g., chemotherapy radiation) prior to administration of the hsp-peptide molecule complexes of the invention. In another specific embodiment, the cancer is a tumor.

The effect of immunotherapy with modified hsp-peptide complexes on progression of neoplastic diseases can be monitored by any methods known to one skilled in the art, including but not limited to measuring: a) delayed hypersensitivity as an assessment of cellular immunity; b) activity of cytolytic T-lymphocytes in vitro; c) levels of tumor specific antigens, e.g., carcinoembryonic (CEA) antigens; d) changes in the morphology of tumors using techniques such as a computed tomographic (CT) scan; e) changes in levels of putative biomarkers of risk for a particular cancer in individuals at high risk, and f) changes in the morphology of tumors using a sonogram. Other techniques that can also be used include scintigraphy and endoscopy.

The preventive effect of immunotherapy using modified hsp-peptide complexes may also be estimated by determining levels of a putative biomarker for risk of a specific cancer. For example, in individuals at enhanced risk for prostate cancer, serum prostate-specific antigen (PSA) is measured by the procedure described by Brawer et al., 1992, J. Urol. 147:841-845, and Catalona et al., 1993, JAMA 270:948-958; or in individuals at risk for colorectal cancer, CEA is measured by methods known in the art; and in individuals at enhanced risk for breast cancer, 16-α-hydroxylation of estradiol is measured by the procedure described by Schneider et al., 1982, Proc. Natl. Acad. Sci. USA 79:3047-3051. The references cited above are incorporated by reference herein in their entirety.

5.8. Prevention and Treatment of Infectious Diseases

It has been discovered also that the modified hsp-peptide complexes of the invention can be prepared from cells infected with an intracellular pathogen as well as cells that have been transformed by an intracellular pathogen. For example, immunogenic hsp peptide complexes may be isolated from eukaryotic cells transformed with a transforming virus such as SV40.

In a preferred aspect of the invention, the purified modified hsp-peptide vaccines may have particular utility in the treatment of human diseases caused by intracellular pathogens. It is appreciated, however, that the vaccines developed using the principles described herein will be useful in treating diseases of other mammals, for example, farm animals including: cattle; horses; sheep; goats; and pigs, and household pets including: cats; and dogs, that similarly are caused by intracellular pathogens.

In accordance with the methods described herein, vaccines may be prepared that stimulate an immune response, in particular a cytotoxic T cell responses, against cells infected with viruses including, but not limited to, hepatitis type A, hepatitis type B, hepatitis type C, influenza, varicella, adenovirus, HSV-I, HSV-II, rinderpest rhinovirus, echovirus, rotavirus, respiratory syncytial virus, papilloma virus, papova virus, cytomegalovirus, echinovirus, arbovirus, huntavirus, coxsachie virus, mumps virus, measles virus, rubella virus, polio virus, HIV-I, and HIV-II. Similarly, vaccines may also be prepared that stimulate cytotoxic T cell responses against cells infected with intracellular bacteria, including, but not limited to, *Mycobacteria, Rickettsia, Mycoplasma, Neisseria* and *Legionella*. In addition, vaccines may also be prepared that stimulate cytotoxic T cell responses against cells infected with intracellular protozoa, including, but not limited to, *Leishmani, Kokzidioa*, and *Trypanosoma*. Furthermore, vaccines may be prepared that stimulate cytotoxic T cell responses against cells infected with intracellular parasites including, but not limited to, *Chlamydia* and *Rickettsia*.

As will be appreciated by those skilled in the art, the protocols described herein may be used to isolate hsp-peptide complexes from any cell genetically manipulated to express a modified hsp, for example, tissues, isolated cells or immortalized eukaryotic cell lines infected with an intracellular pathogen. When immortalized animal cell lines are used as a source of the modified hsp-peptide complex, it is important to use cell lines that can be infected with the pathogen of interest. In addition, it is preferable to use cells that are derived from the same species as the intended recipient of the vaccine. Techniques for introducing an expressible form of the modified hsp gene sequences into these cell lines are described above in Section 5.2.2.

If a pathogen is expected to cause lysis of the host cells, it is preferred to introduce the expressible modified hsp gene sequence into the host cell prior to infecting the cells with the pathogen. For example, in order to prepare a hsp-peptide complex for administration to humans that may be effective against HIV-1, the virus may be propagated in human cells which include, but are not limited to, human CD4+ T cells, HepG2 cells, and U937 promonocytic cells, which have already been transfected with an expressible modified hsp gene sequence. Similarly, influenza viruses may be propagated in, for example, transfected human fibroblast cell lines and MDCK cells, and *mycobacteria* may be cultured in, for example, transfected human Schwaan cells.

The cell supernatant containing secreted modified hsp-peptide complex may be collected just prior to lysis of the host cell.

In another embodiment, if the gene encoding a particular antigenic determinant of a pathogen has been identified, the gene encoding the antigen may be transfected and coexpressed in a human or mammalian cell line together with a modified hsp gene sequence using techniques well known in the art. Such recombinant antigenic cells secreting modified hsp-peptide complexes can be used as a vaccine for injection into a patient to stimulate an immune response against an infected cells or cells bearing the antigen. Autologous recombinant antigenic cells stably expressing and secreting modified hsp-peptide complexes are preferred.

The effect of immunotherapy with modified hsp-peptide complexes on progression of infectious diseases can be monitored by any methods known to one skilled in the art.

6. EXAMPLE

Production of Modified gp96-Ig in Mammalian Cells

A modified hsp, gp96-Ig, was produced by constructing a nucleotide sequence encoding a chimeric protein comprising a gp96 without the retention peptide and the constant regions of murine IgG1, cloning the modified gp96 gene sequence in an expression construct, and transfecting the expression gene construct into a variety of mammalian cells. Methods for constructing the modified hsp gene sequence, making the recombinant cells, and purification of the modified gp96 are described in the following sections.

6.1 Construction of a Modified gp96-Ig Gene Sequence

The coding region of human gp96 is 2,412 bases long, which encodes a signal peptide at the amino terminus (21 amino acid residues), a potential transmembrane region rich in hydrophobic residues, and the endoplasmic reticulum (ER) retention peptide sequence at the carboxyl terminus. The protein has 804 amino acids and an estimated molecular weight of about 96 KD. This coding region was amplified without the sequences encoding the retention sequence, while a sequence encoding the hinge, CH2 and CH3 domains of murine IgG1 was included. The immunoglobulin-based tag facilitates detection by ELISA, purification by affinity chromatography on protein A-Sepharose column and analysis by fluorescent activated cell sorting analysis. A secretory form of a modified gp96 is produced by cells transfected with the modified hsp gene sequence, and the modified gp96 contains bound peptides.

In order to construct a modified gp96 gene sequence, total RNA was extracted with acid guanidinium isothiocyanate-phenol-chloroform extraction from Jurkat cells (a human cell line). Double-stranded cDNA was prepared from the RNA using the GeneAmp RNA PCR Kit (Perkin Elmer Cetus, Norwalk, Conn.), and the coding region of human gp96 was amplified by PCR using Pwo and Taq polymerase of the Expand™ Long Template PCR System (Boehringer Mannheim, Indianapolis, Ind.). PCR cycle conditions were: denaturation of template DNA at 94° C. for 2 min; then 10 cycles at 94° C. for 10 sec, 55° C. for 30 sec and 68° C. for 2 min; and then 25 cycles at 94° C. for 10 sec, 55° C. for 30 sec and 68° C. for 2 min with cycle elongation of 20 sec for each cycle, and a final elongation step at 68° C. for 7 min. The PCR primers used were 5'-ATTACTCGAGGGCCGCACGCCAT-GAGGG-3' which included an XhoI site (forward primer-1, SEQ ID NO:1), and 2) 5'-GCCCGGATCCTTCAGCTGTA-GATTCCTTTGC-3' which included a BamHI site (reverse primer-2, SEQ ID NO:2). The product of the amplification which is a 2.4 kb fragment was purified by agarose gel electrophoresis, cloned into the pCRII vector by TA cloning (Invitrogen, San Diego, Calif.), and then recloned into Bluescript II SK (+/−) phagemid.

The sequence encoding the hinge, CH2 and CH3 domains of murine IgG1 (the Ig tag) was obtained by PCR using as a template murine IgG1 cDNA, or the plasmid, murine IgG1-pCRII. The three cysteine residues in the hinge portion of IgG1 had been mutated to serine residues by standard techniques. The PCR cycle conditions were: denaturation at 95° C. for 2 min; then 30 cycles at 95° C. for 1 min, 50° C. for 1 min and 72° C. for 2 min, and a final elongation step at 72° C. for 10 min. The PCR primers were 5'-GCGAGGATCCGT-GCCCAGGGATTCTGGTTCTAAG-3' which contained a BamHI site (forward primer-3, SEQ ID NO:3), and 5'-CTAAGCGGCCGCAAGGACACTGGGAT-CATTTACCAGG-3' which contained a NotI site (reverse primer-4, SEQ ID NO:4). The PCR product is a 0.68 kb fragment which was purified by agarose gel electrophoresis, cloned into pCRII by TA cloning, and inserted into Bluescript II SK (+/−) phagemid.

To join the cloned modified gp96 to the cloned Ig tag, the sequence encoding gp96 was inserted into the XhoI and BamHI sites of pBluescript, while the Ig tag was inserted into the BamHI and NotI sites of pBluescript. Expression of the fusion protein, gp96-Ig, was confirmed by in vitro coupled transcription/translation (Promega, Madison). Then, the sequence encoding the modified gp96-Ig fusion was cut out with XhoI and NotI, and inserted into the eukaryotic expression vectors, pBCMGSNeo and pBCMGHis, which expresses gp96-Ig under the CMV promoter, and pBMGHis which expresses gp96-IgG under the metallothionein promoter. The size of the modified gp96-Ig sequence was 3.08 kb, and the molecular weight of the secreted chimeric gp96 was estimated to be about 121 kD.

6.2 Production of Modified gp96-Ig In Mammalian Cells

The mouse fibroblast cell line, NIH3T3, the mouse Lewis lung carcinoma cell line, LLC, the mouse mastocytoma cell line, P815, the mouse lymphoma cell line, EL4 and its ovalbumin transfectant, E.G7, the mouse melanoma cell line, B16F10, mouse fibrosarcoma cell line, MC57, and the human small cell lung carcinoma cell lines, SCLC#2 and SCLC#7 were used for expression of the modified gp96-Ig gene sequence. Standard techniques were used to introduce the expression gene constructs into these cells. The episomally maintained, bovine papilloma virus (BPV) based expression vectors pBCMGSNeo or pBCMGHis containing the modified sequence (gp96-Ig-pBCMGSNeo and gp96-Ig-pBC-MGHis) were used to transfect LLC, B16F10, MC57, SCLC#2, and SCLC#7 cells by Lipofectin (GIBCO BRL, Gaithersburg, Md.), NIH3T3 cells by calcium phosphate, and EL4, E.G7 and P815 cells by electroporation. NIH3T3 was cultured in IMDM medium (GIBCO BRL, Grand Island, N.Y.) supplemented with 10% heat-inactivated calf serum (GIBCO BRL). E.G7 and E14 were cultured in IMDM medium supplemented with 10% heat-inactivated FCS (GIBCO BRL) and 50 µM β-mercaptoethanol (Bio-Rad, CA). All other cell lines were cultured in IMDM medium supplemented with 10% heat-inactivated FCS. NIH3T3, MC57, SCLC#2 and SCLC#7 were maintained as monolayer cultures and passaged by short trypsinization with 0.05% trypsin plus EDTA (GIBCO BRL) as required. Transfected cells were selected with 1 mg/ml of G418 (GIBCO) or 2.5 mM of L-Histidinol (Sigma, St. Louis, Mo.) for 2 weeks, and expanded in numbers by dilution and further culturing. Clones that produce large amounts of the secreted gp96-Ig fusion protein were made by limiting dilution.

Untransfected cell lines did not secrete mouse IgG into the culture supernatant, but cell lines transfected with the modified gp96-Ig gene sequence secreted modified gp96.

Cells were plated at $10^6$/ml in AIMV or IMDM with 10% FCS and culture supernatants were harvested at different time points. For analysis of intracellular expression of gp96-Ig, cells were plated similarly, harvested, washed in PBS and lysed by three freeze-thaw cycles. The lysates were centrifuged at 600 g for 10 min and supernatants were centrifuged again at 13,000 g for 60 min. The final supernatant was used to quantitate intracellular expression of gp96-Ig.

The concentration of gp96-Ig in the cell culture media were determined by ELISA using the Ig tag as an antigen. The Ig tag was detected by a labelled anti-mouse antibody. For ELISA, flat-bottom, 96 well plates (Becton Dickinson Labware, Oxnard, Calif.) were coated with goat anti-mouse IgG (5 µg/ml) at 4° C. overnight and blocked with 1% gelatin in PBS at 37° C. for 1 hr. Wells were incubated with culture supernatants or murine IgG (ICN, Costa Mesa, Calif.) as a control at 37° C. for 1 hr and developed with peroxidase-conjugated affinipure F(ab')2 fragment goat anti-mouse IgG (H+L) at 37° C. for 1 hr, followed by incubation with 2,2'-azino-bis(3-ethylbenzthiazoline-6-sulfonic acid) (Sigma). Absorbance was determined with Immunoreader SLT-Labinstruments EAR 400AT (Austria) at a wavelength of 405 nm. Gp96-Ig concentration was determined by comparing its absorbance with that of the murine IgG standard.

TABLE 1

Secretion of gp96-Ig into culture supernatants

| Cell Lines | Gp96-Ig/$10^6$ cells × 24 h |
|---|---|
| SCLC#2 | 140 ng |
| SCLC#7 | 500 ng |
| NIH3T3 | 500 ng |
| EL4 | 160 ng |
| E.G7 | 60 ng |
| P815 | <5 ng |
| LLC | 70 ng |
| B16F10 | 312.5 nga |
| MC57 | 3,300 ng | aMetallothionein promoter

All murine and human cell lines transfected with gp96-Ig in the papilloma virus based episomal expression vectors secreted the fusion protein (FIG. 1a, and Table 1). Mock transfected cells did not secrete gp96-Ig. Under standardized conditions the levels of secreted fusion protein varied depending on the transfectant from 5 ng/ml to 3300 ng/ml.

Secretion of gp96-Ig resulted in its time dependent, linear accumulation in the supernatant (FIG. 2). Intracellular gp96-Ig was detected at a low and constant steady state level in lysates of transfected cells indicating that it does not accumulate in the cell.

6.3 Secretion of gp96-Ig by Mammalian Cells

For staining the membrane of gp96-Ig transfected SCLC cells, goat anti-mouse IgG-FITC or goat anti-rabbit IgG-FITC as a control were used for staining for 15 min at 4° C. and analyzed by a Becton Dickinson FACScan flow cytometer. For intracellular staining, cells were fixed with 4% paraformaldehyde and permeabilized with 1% saponin followed by staining with goat anti-mouse IgG-FITC (Boehringer Mannheim, Indianapolis, Ind.), goat anti-mouse IgG-PE (Southern Biotechnology, Birmingham, Ala.), goat anti-rabbit IgG-FITC or goat anti-syrian hamster IgG-FITC (Jackson ImmunoResearch, West Grove, Pa.) for 15 min at 4° C. and analyzed by a flow cytometer.

FACS analysis of membrane-intact, transfected tumor cells revealed no staining with anti-mouse IgG above background indicating that the Ig moiety of the fusion protein is not displayed on the outer leaflet of the plasma membrane. In contrast, upon permeabilization of the membrane, gp96-Ig is detected intracellularly with a goat anti mouse IgG antibody, but not by control goat anti rabbit IgG antibodies. The transmembrane domain of gp96 does not interfere with the secretion of gp96-Ig and does not lead to intracellular accumulation. These data are consistent with previous reports suggesting that the transmembrane domain is not used for anchoring of gp96 in the membrane and that gp96 is not an integral membrane protein.

6.4 Purification of Modified gp96-Ig

Gp96-Ig was purified by affinity chromatography on a Protein A column (Bio-Rad, Hercules, Calif.). Spent serum-free culture medium from gp96-Ig-transfected SCLC#7 (SCLC#7-gp96-Ig) was used as a source for the purification of the Ig fusion protein. Gp96-Ig transfected NIH-3T3 cells were plated at $10^6$/ml in AIMV and culture supernatants were harvested after 6-8 days. After removal of cellular debris by centrifugation and filtration, whole protein of the supernatant was concentrated by ammonium sulfate precipitation (55% saturation) and dialyzed against PBS. Samples were diluted 1:2 with 3.5 M NaCl, 1.6 M glycine, pH 9.0 (binding buffer) and applied to the Protein A column. The column was washed thoroughly with binding buffer, and bound protein was eluted with 0.1M citric acid, pH 6.5. Fractions containing protein were pooled and dialyzed against PBS. Concentration of gp96-Ig was determined by the Micro BCA Protein Assay Reagent Kit (Pierce, Rockford, Ill.).

Sodium dodecyl sulfate polyacrylamide gel electrophoresis (SDS-PAGE) was performed on 4-15% Tris-Glycine gels (Bio-Rad), and stained with Coomassie Blue. For Western blotting, proteins on SDS-PAGE were blotted to nitrocellulose, and probed with a rat monoclonal antibody specific for Grp94 (9G10; StressGen, Victoria, Canada) followed by peroxidase-conjugated affinipure F(ab')2 fragment goat anti-rat IgG (H+L) (Jackson ImmunoResearch, PA).

When gp96-Ig purified by protein A chromatography was analyzed by SDS-PAGE, the material migrated as a major band of the predicted molecular weight of 120 kD, and two minor higher molecular bands, previously reported also for unmodified gp96 (FIG. 1b). Western blotting with a monoclonal antibody specific for gp96 confirmed the identity of the fusion protein. Only the major band was stained suggesting that the minor bands are glycosylation variants of gp96 not recognized by the antibody.

Secreted modified gp96-Ig molecules were also analyzed by sodium dodecyl sulfate-polyacrylamide gel electrophoresis (SDS-PAGE) under reducing and non-reducing conditions. FIG. 1C shows a comparison of purified gp96-Ig molecules secreted by SCLC#2, murine IgG, and a fusion protein of CD30 and the Ig peptide tag. The gp96-Ig fusion protein comprising gp96 (96 kD) and the Ig tag (25 kD) appears at the appropriate size range. The triplets representing modified gp96-Ig in both the reduced and non-reduced fractions had previously been described for gp96.

7. EXAMPLE

Tumorigenicity of Tumor Cells that Produce Modified gp96-Ig

According to the invention, recombinant tumor cells secreting modified hsp-peptide complexes are useful as vaccines. The in vivo immunogenicity of such recombinant cells was tested by assessing their tumorigenicity in animals that do not have any pre-existing tumors.

Recombinant tumor cells were injected into mice to determine whether the tumorigenicity of such recombinant cells have been reduced relative to unmodified tumor cells of the same type (i.e., without the expression gene construct). The following results indicate that these recombinant tumor cells are less active than the original tumor cells in forming tumors in the test animals. It suggests that the immune system of these animals have mounted an effective immune response against such cells that are more immunogenic and/or antigenic than the original tumor cells. Tumor cells that persisted in test animals originally injected with recombinant tumor cells were isolated and returned to culture. The observation that these tumor cells ceased to secrete the modified hsp-Ig molecules suggest that these tumor cell were selected variants and were not effectively targeted by the immune effector mechanisms.

7.1 Comparison of Relative Tumorigenicity of E.G7 and E.G7-gp96-Ig

Two groups of C57BL/6 mice were respectively injected subcutaneously with the indicated number of live E.G7 and E.G7-gp96-Ig tumor cells. The results are shown in Table 2.

TABLE 2

| No. of cells used | Mice with tumor | |
|---|---|---|
| for injection | E.G7 | E.G7-gp96-Ig |
| $1 \times 10^7$ | 2/2 | 1/7 |
| $1 \times 10^6$ | 20/23 | 1/5 |
| $1 \times 10^5$ | 4/10 | 0/2 |

Almost all mice in which E.G7 were injected had developing tumors. However, E.G7-gp96-Ig tumors were rejected in most of the mice. This suggests that the modified gp96 secreted from E.G7-gp96-Ig holds tumor peptides of E.G7 and can induce tumor immunity against E.G7. Tumors were excised from 2 mice with E.G7-gp96-Ig tumors and returned to culture medium. These tumor cells did not secrete modified gp96-Ig in culture. We believe that these tumor variants which have lost the ability to secrete modified gp96-Ig were selected in vivo.

7.2 Comparison of Relative Tumorigenicity of EL4 and EL4-gp96-Ig

Two groups of C57BL/6 mice were respectively injected subcutaneously with the indicated number of live EL4 and EL4-gp96-Ig tumor cells. The results are shown in Table 3.

TABLE 3

| No. of cells used | Mice with tumor | |
|---|---|---|
| for injection | EL4 | EL4-gp96-Ig |
| $1 \times 10^6$ | 2/2 | 3/5 |
| $1 \times 10^5$ | 7/7 | 2/5 |
| $1 \times 10^4$ | 9/10 | 2/5 |

Almost all mice in which EL4 were injected had developing tumors. However, EL4-gp96-Ig tumors were rejected in almost 50% of the injected mice. This observation suggests that gp96 secreted from EL4-gp96-Ig holds tumor peptides of EL4 and can induce tumor immunity against EL4 cells. Tumors were excised from 3 mice with EL4-gp96-Ig tumors and returned to culture medium. Similarly, these tumor variants stopped secreting modified gp96-Ig suggesting that they escaped the immune effector mechanisms in vivo.

7.3 Comparison of Relative Tumorigenicity of MC57 and MC57-gp96-Ig

C57BL/6 mice were injected subcutaneously with the indicated number of liver tumor cells. All of the mice in which MC57 were injected survived without tumor. However, one mice in which MC57-gp96-Ig cells were injected had developing tumors. The tumor were excised and returned to culture medium. The level of modified gp96-Ig molecules in the culture supernatant of excised tumor had decreased to 100 µg/ml.

TABLE 4

| No. of cells used | Mice with tumor | |
|---|---|---|
| for injection | MC57 | MC57-gp96-Ig |
| $1 \times 10^7$ | 0/4 | 1/2 |
| $3 \times 10^6$ | 0/2 | 0/2 |
| $1 \times 10^6$ | 0/2 | 0/2 |

7.4 Comparison of Relative Tumorigenicity of B16F10 and B16F10-gp96-Ig

Two groups of C57BL/6 mice were respectively injected subcutaneously with the indicated number of live B16F10 and B16F10-gp96-Ig tumor cells. All of the mice in which B16F10-gp96-Ig cells were injected did not reject the tumor. Two mice injected with $1 \times 10^4$ BF6F10 cell rejected the tumor.

TABLE 5

| No. of cells used | Mice with tumor | |
|---|---|---|
| for challenge | B16F10 | B16F10-gp96-Ig |
| $1 \times 10^6$ | 2/2 | 2/2 |
| $1 \times 10^5$ | 2/2 | 2/2 |
| $1 \times 10^4$ | 0/2 | 2/2 |

7.5 Tumorigenicity of E.G7-gp96-Ig and LLC-gp96-Ig

Two cell lines were selected for further in vivo study. E.G7 is an ovalbumin transfectant of the EL4 lymphoma. E.G7 forms lethal tumors in C57BL/6 mice despite its relative immunogenicity. Gp96-Ig transfection of E.G7 allows the determination whether E.G7-gp96-Ig immunization immunizes against either or both, EL4 associated antigens and the ovalbumin-surrogate antigen. The second tumor, LLC transfected with sequences encoding gp96-Ig or ovalbumin was used because, in contrast to E.G7, it is a non-hematopoietic, low-immunogenic tumor. Both cell lines secrete comparable amounts of gp96-Ig (See Table 1).

Tumorigenicity in vivo was determined by subcutaneous injection of live tumor cells in 200 µl PBS into the flanks of mice. The size of tumors was measured in two dimensions twice weekly for at least 2 months. When mean tumor growth exceeded 10 mm diameter after 3 weeks, the mice were categorized as tumor positive and sacrificed. Mice were immunized by subcutaneous injection of $10^6$ live E.G7-gp96-Ig or irradiated E.G7 as a control (in 200 μl PBS), given in the right flank. Two immunizations at 2 weeks intervals were given.

Gp96-Ig secretion decreases the tumorigenicity of E.G7 in C57BL/6 mice by more than a hundred fold when compared to mock transfected or untransfected E.G7. Subcutaneous inoculation of ten million heat shock protein secreting tumor cells caused tumors in only 10% of the inoculated mice (FIG. 3). A similar reduction of tumorigenicity by gp96-Ig secretion was observed with EL4. Gp96-Ig secretion by LLC resulted in a more moderate, about five fold decrease of tumorigenicity (FIG. 3). These results suggest that secretory gp96-Ig decreased tumorigenicity of tumors possibly by increasing their immunogenicity.

8. EXAMPLE

Protective Effect of Vaccination with Cells Expressing Modified gp96-Ig

In order to demonstrate the ability of recombinant tumor cells that are producing modified gp96-Ig to stimulate a protective immune response, mice were first vaccinated with recombinant tumor cells, and then challenged with an injection of tumor cells not containing the modified gp96-Ig gene construct.

Groups of mice were immunized by subcutaneous injection of $1\times10^6$ of live E.G7-gp96-Ig, given in the right flank. Two immunizations at 2 weeks intervals were given. Mice were then challenged by subcutaneous injections in the left flank of the indicated number of live E.G7 or EL4 cells weeks after the last immunization. E.G7 cells are EL4 ells transfected with an ovalbumin gene construct.

TABLE 6

| No. of cells used | Mice with tumor | |
| for challenge | E.G7-gp96-Ig | Unvaccinated |
|---|---|---|
| E.G7 | | |
| $3 \times 10^6$ | 5/5 | ND |
| $1 \times 10^6$ | 2/6 | 20/23 |
| $8 \times 10^5$ | 0/4 | 3/3 |
| EL4 | | |
| $1 \times 10^5$ | 4/5 | 7/7 |
| $3 \times 10^4$ | 3/4 | 2/2 |
| $1 \times 10^4$ | 1/5 | 9/10 |
| $3 \times 10^3$ | 0/5 | 3/5 |

The results in Table 6 show that fewer mice vaccinated with recombinant E.G7-gp96-Ig cells developed E.G7 and EL4 tumors, and thus indicate that such recombinant tumor cells can be used prophylactically to prevent or reduce the incidence of specific antigenically-related tumors.

8.1 Protective Effect of E.G7-gp96-Ig Against E.G7 and LLC Tumor Cells

The cell lines E.G7 and LLC were selected for further in vivo studies. As described above, mice were immunized by subcutaneous injection in the right flank of non-irradiated E.G7 cells secreting gp96-Ig. Two immunizations at 2 weeks intervals were given. Subsequently they were challenged with untransfected or mock transfected E.G7, with EL4, with untransfected LLC and with LLC-ova. To make LLC-ova, chicken ovalbumin gene cloned into expression vector, pAc-NEO-OVA, was used to transfect LLC by Lipofectin (GIBCO BRL). Transfected cells were selected with 1 mg/ml of G418 (GIBCO BRL) for at least 2 weeks and their secretion levels were tested by ELISA. Mice immunized with irradiated E.G7 and unvaccinated mice served as vaccination controls.

The results are shown in FIG. 4. E.G7-gp96-Ig immunized mice were protected against a ten fold higher challenge dose with E.G7 than unimmunized mice or mice vaccinated with irradiated cells. The effect of immunization was even more pronounced when challenged with EL4, allowing a fifty fold dose increase of challenge compared to the controls. As expected, EG7-gp96-Ig immunization offered no protection against challenge with untransfected or vector transfected LLC while a moderate, about threefold increase in protection was observed when ovalbumin transfected LLC were used. The strong protection of EG7-gp96-Ig immunized mice against EL4 challenge may be due to multiple tumor antigens shared by EG7 and EL4. In contrast, the weak protection obtained with LLC-ova depends on T cells recognizing a single or limited number of epitopes derived from ovalbumin and presented by $H2^b$ molecules.

9. EXAMPLE

In Vivo Depletion or Inactivation of Competent Immune Cells in Inoculated Animals The involvement of immune mechanisms in the rejection of EG7-gp96-Ig was further examined by in vivo depletion or inactivation of competent immune cells.

Monoclonal antibodies used for in vivo depletion of the CD4+ and CD8+ cell subsets were GK1.5 and 2.43, respectively. They were purified from hybridoma supernatants followed by Protein G affinity chromatography. 100 μg of GK1.5 or 2.43 in 200 μl PBS were administered by intraperitoneal injection, 2 days prior to or 3 days after subcutaneous inoculation of $10^6$ live E.G7-gp96-Ig (in 200 μl PBS). Depletion of CD4 and CD8 cells was verified by FACS analysis. For functional inhibition of macrophages, 1 mg of carrageenan (type II; Sigma) in 200 μl PBS was administered by intraperitoneal injection.

One million tumor cells secreting gp96-Ig were inoculated into an animal, a dose sufficient to establish tumors that grow to a mean of about 8 mm diameter and subsequently shrink and are rejected. Tumor rejection is blocked in mice treated with the anti CD8 antibody 2.43, either two days prior to or three days after tumor inoculation (FIG. 5). The anti CD4 antibody GK1.5 had no effect on tumor rejection regardless of time of injection, even though it completely depleted CD4 cells for more than 14 days. Similarly Carrageenan, known to inactivate macrophages in vivo, had no effect on tumor rejection.

These data are consistent with the explanation that peptides associated with secreted gp96-Ig are presented by class I MHC and stimulate a tumor specific CD8+ CTL response leading to tumor rejection. This response appears to be independent of CD4 help and does not require macrophages. Udono et al. (1994, Proc. Natl. Acad. Sci. USA. 91:3077-3081), using soluble gp96 purified from Meth A tumor cells for immunization, reported a requirement for CD8 cells and macrophages in the priming phase and a requirement for CD4 and CD8 cells as well as macrophages in the effector phase of tumor rejection of Meth A tumors. In our model system, gp96-Ig is secreted by live tumor cells and serves to immunize the mouse resulting in the subsequent rejection of the tumor. Tumor growth began to slow by day 6 to 8 indicating that anti tumor immunity had been initiated and tumors were rejected within the subsequent week. CD4 cells and macrophages were not required for tumor rejection, regardless of the time of their depletion, two days prior to or three days after tumor inoculation. This indicates that CD4 cells and macrophages are not essential for induction of immunity nor are they required in the effector phase in this tumor system. CD8 cells on the other hand are critically important in all phases of the response to secretory gp96-Ig.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

secreted by a cell in which it is expressed and non-covalently associated with an antigenic peptide, (ii) lacks an endoplasmic reticulum retention sequence present in the unmodified heat shock protein, and (iii) comprises a peptide tag comprising constant regions of an immunoglobulin heavy chain and wherein the modified heat shock protein gene sequence is operably linked to at least one regulatory region that controls expression of the modified heat shock protein gene in the cancer cells; and (b) administering to the individual the human cancer cell comprising the modified heat shock protein gene sequence to elicit an immune response to the tumor antigen.

2. A method of eliciting an immune response to a tumor antigen in an individual having a cancer for the purpose of

What is claimed is:

1. A method of eliciting an immune response to a tumor antigen in an individual having a cancer for the purpose of treating the cancer comprising: (a) obtaining a human cancer cell comprising the tumor antigen and introducing a modified heat shock protein gene sequence into the human cancer cell, wherein the modified heat shock protein gene sequence encodes a modified gp96 heat shock protein which (i) is secreted by a cell in which it is expressed and non-covalently associated with an antigenic peptide, (ii) lacks an endoplasmic reticulum retention sequence present in the unmodified heat shock protein, (iii) comprises a leader peptide not present in the unmodified heat shock protein, and (iv) comprises a peptide tag comprising constant regions of an immunoglobulin heavy chain, and wherein the modified heat shock protein gene sequence is operably linked to at least one regulatory region that controls expression of the modified heat shock protein gene in the cancer cells; and (b) administering to the individual the human cancer cell comprising the modified heat shock protein gene sequence to elicit an immune response to the tumor antigen.

3. A method of eliciting an immune response to a tumor antigen in an individual having cancer for the purpose of treating the cancer comprising administering to the individual a cancer cell engineered to secrete an immunogenic complex comprising a modified gp96 heat shock protein non-covalently associated with an antigenic peptide of the tumor antigen to elicit an immune response to the tumor antigen, wherein the modified gp96 heat shock protein (i) comprises a peptide tag comprising constant regions of an immunoglobulin heavy chain, and (ii) lacks an endoplasmic reticulum retention sequence present in the unmodified heat shock protein.

4. The method of claim 1, wherein the gene sequence encoding the modified gp96 heat shock protein is expressed by a vector based on bovine papilloma virus.

5. The method of claim 1 in which the cancer is lung carcinoma or small cell lung carcinoma.

6. The method of claim 1, wherein the unmodified heat shock protein is human gp96.

7. The method of claim 1, wherein the human cancer cell is obtained from another individual than the one to whom the human cancer cell is administered.

8. The method of claim 2, wherein the gene sequence encoding the modified gp96 heat shock protein is expressed by a vector based on bovine papilloma virus.

9. The method of claim 2 in which the cancer is lung carcinoma or small cell lung carcinoma.

10. The method of claim 2, wherein the unmodified heat shock protein is human gp96.

11. The method of claim 2, wherein the human cancer cell is obtained from another individual than the one to whom the human cancer cell is administered.

12. A method of eliciting an immune response to a tumor antigen in an individual having a cancer for the purpose of treating the cancer comprising administering to the individual an injectable dose of a vaccine, the vaccine comprising recombinant cancer cells engineered to secrete complexes of a modified gp96 heat shock protein and an antigenic peptide of the tumor antigen in a sufficient amount to cause activation of a CD4-independent, CD8 T lymphocyte response against the tumor antigen, wherein the modified gp96 heat shock protein (i) comprises a peptide tag comprising constant regions of an immunoglobulin heavy chain, and (ii) lacks an endoplasmic reticulum retention sequence present in the unmodified heat shock protein.

13. The method of claim 12, wherein the recombinant cancer cells have been irradiated to eliminate their proliferation while maintaining their ability to secrete the modified gp96 heat shock protein-antigenic peptide complexes for 7-10 days.

14. A method of eliciting an immune response to a tumor antigen in an individual having a cancer for the purposes of treating the cancer comprising administering to the individual an injectable dose of a vaccine, the vaccine comprising recombinant cancer cells engineered to secrete complexes of a modified heat shock protein and an antigenic peptide of the tumor antigen, wherein the modified heat shock protein is a modified human gp96 protein that lacks an endoplasmic reticulum retention sequence but retains the ability to bind antigenic peptides specifically and non-covalently and to present such bound peptides to immune cells in the course of antigen presentation, wherein the recombinant cancer cells have been irradiated prior to administration to the individual, and wherein the step of administering the vaccine elicits the immune response to the tumor antigen in the individual.

15. The method of claim 14, wherein the modified human gp96 protein that lacks the endoplasmic reticulum retention sequence comprises all other amino acid sequences present in the unmodified human gp96 protein.

16. The method of claim 14, wherein the recombinant cancer cells are allogeneic to the individual.

* * * * *

UNITED STATES PATENT AND TRADEMARK OFFICE
CERTIFICATE OF CORRECTION

PATENT NO. : 8,685,384 B2
APPLICATION NO. : 11/878460
DATED : April 1, 2014
INVENTOR(S) : Podack et al.

Page 1 of 2

It is certified that error appears in the above-identified patent and that said Letters Patent is hereby corrected as shown below:

On the title page

Page 2, Item [56] References Cited – OTHER PUBLICATIONS, Col. 2, Line 11:
After "Ig," The", delete "FASER" and insert -- FASEB --.

Page 2, Item [56] References Cited – OTHER PUBLICATIONS, Col. 2, Line 16:
After "Escherichia", delete "coil" and insert -- coli --.

Page 2, Item [56] References Cited – OTHER PUBLICATIONS, Col. 2, Line 46:
After "genome of", delete "mammalain" and insert -- mammalian --.

Page 2, Item [56] Col. 2, Line 47:
After "gene and the", delete "IoxP" and insert -- loxP --.

Page 2, Item [56] Col. 2, Line 55:
After "characterization of an", delete "immunosuppresive" and insert -- immunosuppressive --.

Page 3, Item [56] Col. 2, Line 17:
After "1988", delete "Chromosonal" and insert -- Chromosomal --.

Page 4, Item [56] Col. 2, Line 12:
After "Vaccines", delete "forthe" and insert -- for the --.

Signed and Sealed this
Fourteenth Day of October, 2014

Michelle K. Lee
*Deputy Director of the United States Patent and Trademark Office*

CERTIFICATE OF CORRECTION (continued)
U.S. Pat. No. 8,685,384 B2

Page 4, Item [56] Col. 2, Line 56:

After "Arnold et al", delete ""Inflences" and insert -- Influences --.

In the Claims

Column 52, Line 6, claim 12, delete "gp96heat" and insert -- gp96 heat --.

```
                      SEQUENCE LISTING

<160> NUMBER OF SEQ ID NOS: 4

<210> SEQ ID NO 1
<211> LENGTH: 28
<212> TYPE: DNA
<213> ORGANISM: Artificial Sequence
<220> FEATURE:
<223> OTHER INFORMATION: primer

<400> SEQUENCE: 1
attactcgag ggccgcacgc catgaggg                                      28

<210> SEQ ID NO 2
<211> LENGTH: 31
<212> TYPE: DNA
<213> ORGANISM: Artificial Sequence
<220> FEATURE:
<223> OTHER INFORMATION: primer

<400> SEQUENCE: 2
gcccggatcc ttcagctgta gattcctttg c                                  31

<210> SEQ ID NO 3
<211> LENGTH: 34
<212> TYPE: DNA
<213> ORGANISM: Artificial Sequence
<220> FEATURE:
<223> OTHER INFORMATION: primer

<400> SEQUENCE: 3
gcgaggatcc gtgcccaggg attctggttc taag                               34

<210> SEQ ID NO 4
<211> LENGTH: 37
<212> TYPE: DNA
<213> ORGANISM: Artificial Sequence
<220> FEATURE:
<223> OTHER INFORMATION: primer

<400> SEQUENCE: 4
ctaagcggcc gcaaggacac tgggatcatt taccagg                            37
```